US 9,605,404 B2

(12) United States Patent
Hale et al.

(10) Patent No.: US 9,605,404 B2
(45) Date of Patent: Mar. 28, 2017

(54) HIGH STRAIN DYNAMIC LOAD TESTING PROCEDURE

(71) Applicants: Glen G. Hale, Easton, PA (US); Charles J. Kelleher, Flemington, NJ (US)

(72) Inventors: Glen G. Hale, Easton, PA (US); Charles J. Kelleher, Flemington, NJ (US)

(*) Notice: Subject to any disclaimer, the term of this patent is extended or adjusted under 35 U.S.C. 154(b) by 323 days.

(21) Appl. No.: 14/289,600

(22) Filed: May 28, 2014

(65) Prior Publication Data

US 2014/0352449 A1   Dec. 4, 2014

Related U.S. Application Data

(63) Continuation-in-part of application No. 14/289,584, filed on May 28, 2014, now Pat. No. 9,458,593.

(60) Provisional application No. 61/828,599, filed on May 29, 2013.

(51) Int. Cl.

| | |
|---|---|
| *E02D 33/00* | (2006.01) |
| *E02D 27/48* | (2006.01) |
| *E02D 5/38* | (2006.01) |
| *E02D 7/02* | (2006.01) |
| *G01N 3/303* | (2006.01) |
| *G01M 5/00* | (2006.01) |

(52) U.S. Cl.
CPC ............. *E02D 33/00* (2013.01); *E02D 5/38* (2013.01); *E02D 7/02* (2013.01); *G01M 5/0058* (2013.01); *G01N 3/303* (2013.01); *E02D 27/48* (2013.01)

(58) Field of Classification Search
CPC ........ E02D 35/005; E02D 35/00; E02D 27/48
USPC ......................................................... 405/230
See application file for complete search history.

(56) References Cited

U.S. PATENT DOCUMENTS

| | | |
|---|---|---|
| 3,852,970 A | 12/1974 | Cassidy |
| 4,347,743 A | 9/1982 | Rausche et al. |
| 4,695,203 A | 9/1987 | Gregory |
| 5,018,905 A | 5/1991 | Kinder |
| 5,123,209 A | 6/1992 | Nally |
| 5,176,472 A | 1/1993 | Kinder |
| 5,355,715 A | 10/1994 | Rausche et al. |
| 5,575,591 A | 11/1996 | Vanderklaauw |

(Continued)

*Primary Examiner* — Frederick L Lagman
(74) *Attorney, Agent, or Firm* — Madson IP, P.C.

(57) ABSTRACT

A method is provided for using low-overhead equipment to perform a dynamic load test on pipe piles of a deep pile foundation for an existing building. The existing building is lifted to a predetermined elevation above grade and cribbing stacks are positioned to support the existing building at the predetermined elevation above grade. The cribbing stacks are spaced from each other enabling low-overhead equipment to maneuver underneath the elevated building to drill drive pipe piles and to position a drop weight used for dynamic load testing the driven pipe piles. Grout is pumped under pressure into the pipe piles continuously during the drill driving of the pipe piles so that grout exits through a grout port to mix with disturbed soil about the pipe pile to encase the pipe pile in a grout-soil mixture. Sensors are attached to the pipe pile being tested. The sensors provide information regarding the pipe pile impacted by the drop weight. Bearing capacity and other pipe pile characteristics that indicate whether the pipe pile tested is acceptable are determined from the information provided by the sensors.

20 Claims, 16 Drawing Sheets

(56) References Cited

U.S. PATENT DOCUMENTS

| | | | |
|---|---|---|---|
| 5,904,447 A | 5/1999 | Sutton et al. | |
| 5,934,836 A | 8/1999 | Rupiper et al. | |
| 5,978,749 A | 11/1999 | Likins, Jr. et al. | |
| 5,980,160 A | 11/1999 | Vanderklaauw | |
| 6,301,551 B1 | 10/2001 | Piscalko et al. | |
| 6,379,085 B1 | 4/2002 | Vanderklaauw | |
| 6,684,577 B2 | 2/2004 | Dimitrijevic | |
| 6,821,056 B1 | 11/2004 | Mansour | |
| 6,923,599 B2 | 8/2005 | Kelso | |
| 6,971,821 B1 | 12/2005 | Mansour et al. | |
| 7,097,388 B1 | 8/2006 | Mansour et al. | |
| 7,967,531 B2 | 6/2011 | Collina et al. | |
| 8,161,823 B2 | 4/2012 | Berris, Jr. et al. | |
| 8,382,369 B2 | 2/2013 | Piscalko et al. | |
| 8,612,175 B2 | 12/2013 | Dalton et al. | |
| 8,708,559 B2 | 4/2014 | Piscsalko et al. | |
| 2004/0037653 A1 | 2/2004 | Kelso | |
| 2006/0067794 A1 | 3/2006 | Mitchell | |
| 2009/0026430 A1 | 1/2009 | McDonald et al. | |
| 2009/0263189 A9 * | 10/2009 | Koivunen | E02D 5/523 403/379.4 |
| 2012/0114423 A1 * | 5/2012 | Zago | E02D 35/00 405/230 |
| 2012/0155968 A1 | 6/2012 | Byun et al. | |
| 2012/0203462 A1 * | 8/2012 | Dalton | E02D 7/00 702/5 |
| 2014/0356076 A1 * | 12/2014 | Hale | E02D 5/223 405/255 |

* cited by examiner

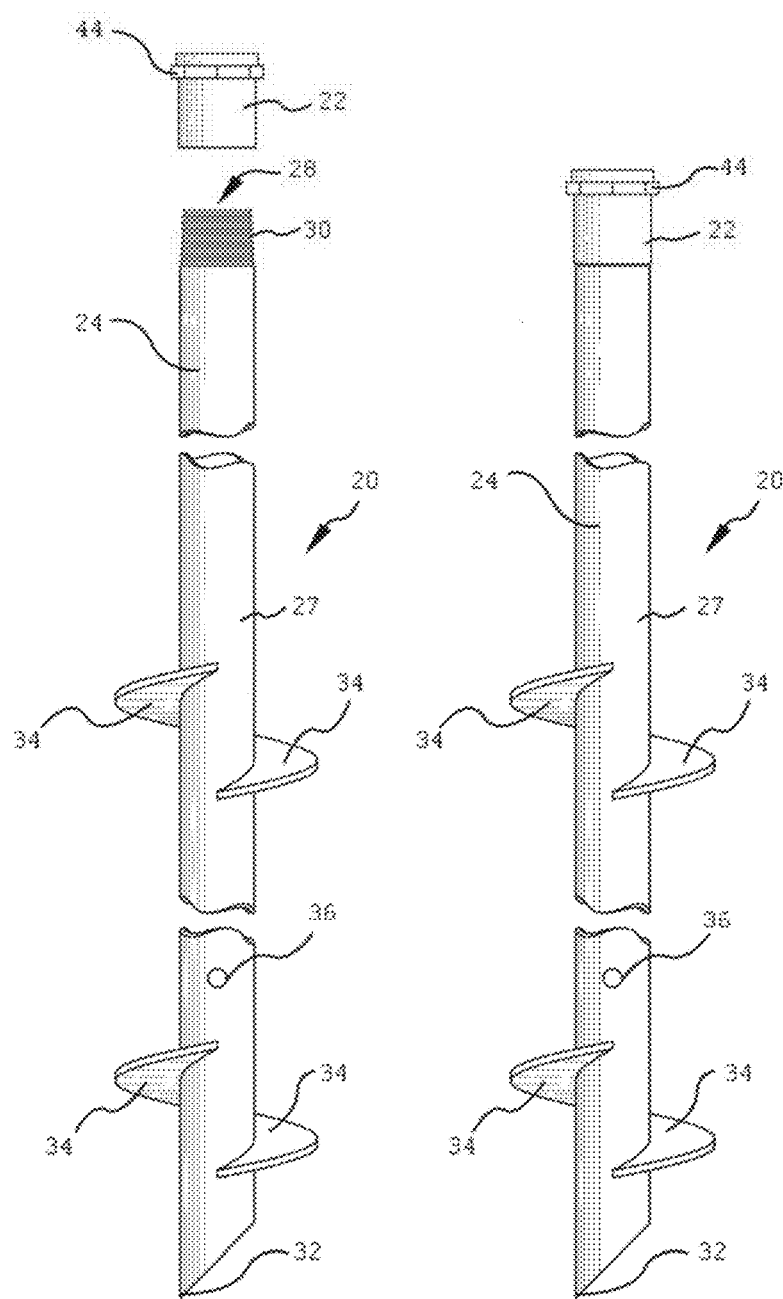

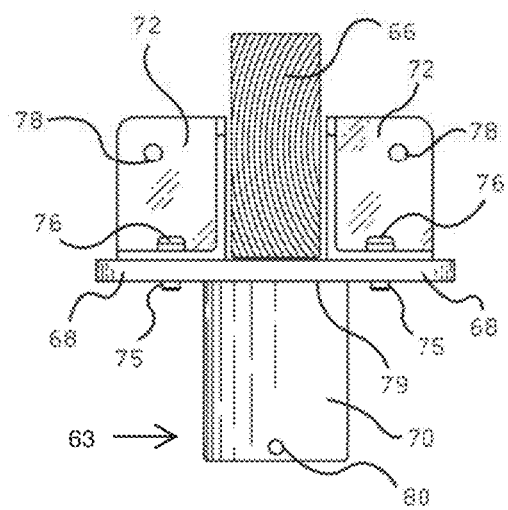
FIG. 12C
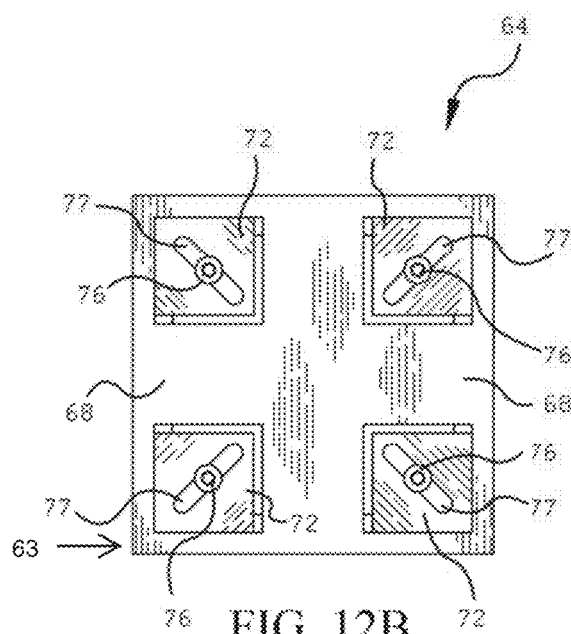
FIG. 12B
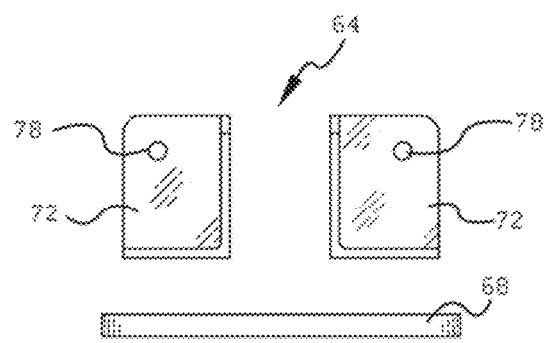
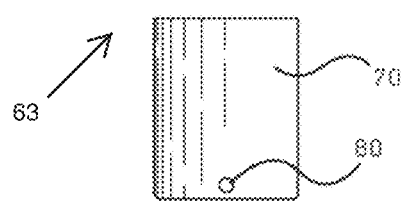
FIG. 12A

HIGH STRAIN DYNAMIC LOAD TESTING PROCEDURE

BACKGROUND OF THE INVENTION

1. Related Application

This patent application is a continuation-in-part of U.S. patent application Ser. No. 14/289,584 now U.S. Pat. No. 9,458,593 titled "Deep Pile Foundation Construction Methodology for Existing and New Buildings" and also claims the benefit of U.S. Provisional Patent Application Ser. No. 61/828,599 that was filed on May 29, 2013, for an invention titled "Deep Pile Foundation Construction Methodology for Existing Residential Homes." The aforementioned patent application and provisional patent application are expressly incorporated into this application by this reference.

2. Field of the Invention

The present invention relates to systems and methods for dynamic load testing pipe piles drill driven to serve in a deep pile foundation. More specifically, the present invention relates to systems and methods for dynamic load testing pipe piles drill driven underneath a lifted residential house or building under low-overhead conditions.

3. The Relevant Technology

Revised FEMA (Federal Emergency Management Agency)/NFIP (National Flood Plan Insurance Program) requirements (2012-2013; pending finalization in 2014) will require hundreds of thousands of residential houses, in United States coastal flood hazard zones, to be lifted and placed onto elevated foundations in order to qualify for NFIP coverage. Presently, the conventional industry standard process for lifting a residential house and placing it onto an elevated concrete block or a helical micropile foundation, with a two-to-six foot deep concrete grade berm, has a cycle time of approximately 28 days.

Coastal construction requirements are different from inland construction. Flood levels, velocities, and wave action in coastal areas tend to make coastal flooding more damaging than inland flooding. Further, coastal erosion can undermine buildings and destroy land, roads, utilities, and infrastructure. Wind speeds are typically higher in coastal areas and require stronger engineered building connections and more closely spaced nailing of building sheathing, siding, and roof shingles. Wind-driven rain, corrosion, and decay are also frequent concerns in coastal areas.

In general, buildings in coastal areas must be designed and built to withstand higher loads and more extreme conditions. Buildings in coastal areas also require more maintenance and upkeep. Coastal buildings must be designed to withstand coastal forces and conditions. Coastal buildings must be built as designed and sited so that erosion does not undermine the building or render it uninhabitable. A well-built but poorly sited building can be undermined. Even if a building is set back or situated farther from the coastline, it must be capable of resisting high winds and other hazards that may occur at the site.

Using recommended building practices for constructing new homes in coastal area is important and may avoid many future problems. For example, building at a site away from eroding shorelines and high-hazard areas is advisable. Also, flat or low-sloped porch roofs, overhangs, and gable ends are subject to increases uplift in high winds. Buildings that are both tall and narrow are subject to overturning. Each of these problems may be avoided through the design process by making the building more resistant to high winds.

To qualify for flood insurance, the lowest floor must be elevated above the Design Flood Elevation (DFE), i.e., the bottom of the lowest horizontal structural member supporting the lowest floor must be above the DFE. Also, an open foundation is required in certain flood hazard zones, i.e., VE zones, and may not be obstructed below the elevated portion of the building. Further the foundation must be deep enough to resist the effects of scour and erosion, i.e., strong enough to resist wave, current, flood, and debris forces and capable of transferring wind and seismic forces on upper stories to the ground.

Additionally, the connection of the walls and floor to the foundation must be sound and any building materials below the DFE should be flood-resistant materials. All exposed materials should be moisture-resistant and decay-resistant and any metals should have enhanced corrosion protection.

These and other recommended building practices are advisable for new building construction in coastal areas. Needless to say, for existing homes and other buildings in coastal area, the new FEMA/NFIP requirements present difficult and serious problems. Existing homes may be rendered uninhabitable and/or ineligible for flood insurance. On the other hand, flood insurance premiums may be reduced by up to 60% by exceeding minimum siting, design, and construction practices.

As noted above, hundreds of thousands of existing buildings must be lifted and placed unto elevated foundations that comply with the requirements to qualify for flood insurance. The challenges to placing an existing structure (residential home or business building) onto requirement-compliant foundation include constructing the foundation underneath the lifted structure where there may be low ceiling tolerance, load testing one or more of the pipe piles of the foundation, and securing the foundation to the lifted structure.

Accordingly, a need exists for a new system and method for time- and cost-effectively lifting and securing existing homes onto foundations that are requirement compliant and may withstand flood conditions better than traditional timber, helical or block foundations. Such systems and methods are disclosed herein.

BRIEF SUMMARY OF THE INVENTION

The exemplary embodiments of the present invention have been developed in response to the present state of the art, and in particular, in response to the problems and needs in the art that have not yet been fully solved by currently available technology.

This invention involves deep pile foundation construction methodology for existing residential homes and other buildings and may also involve deep pile foundation construction for homes and other buildings under construction. The methodology involves dynamic load testing installed pressure grouted displacement piles ("PGD piles) in the deep pile foundation under low-overhead or open site conditions. Such dynamic load testing enables that the PGD piles may be used in the deep pile foundation by capping each PGD pile with a pile cap connector that may be secured to the existing home or other building. Further, the PGD piles may be placed at any of the locations that they may be drill driven. The method of the present invention is particularly suitable for testing each and all of the PGD piles used for retrofitting elevated foundations to homes or other buildings that must be lifted and placed onto elevated foundations in order to qualify for NFIP coverage. The preparation steps and dynamic load testing may also be used for open site construction.

Whereas, the present conventional, industry standard process for lifting a residential home and placing it onto an elevated concrete block or helical micropile foundation, with a two-to-six foot deep concrete grade berm, takes approximately 28 days to complete, the construction method reduces the cycle time for lifting and anchoring a residential home onto a foundation to approximately 7 to 10 days and provides a sturdier, more durable foundation than conventional methods, allowing for dynamic load testing of any of the PGD piles included in the foundation without disrupting the construction timetable.

Prior to installation of the PGD piles, the site should be made ready for installation. For an existing home or building, the utilities are disconnected and the home or building is lifted onto stable stacks of wood cribbing using standard industry practices so that the lowest part of the home or building is approximately 10 to 12 feet above grade. The cribbing should be spaced so that the low-overhead equipment (e.g., a skid steer or a post driver) may maneuver between the cribbing stacks. Typically, a distance of 80 to 90 inches will be sufficient distance between cribbing stacks to allow low-overhead equipment to maneuver under the base of the elevated home or building. A soil boring should be performed to a depth specified by the engineer on the site so that the engineer may determine the specific locations for each of the PGD piles needed to support the existing home or building or the home or building under construction. Any existing foundation should be demolished and removed so that the site may be cleared of all construction debris and the ground surface may be leveled and worked to support low-overhead equipment. The locations for the piles may be measured and paint-marked on suitable grade as determined by proper surveying equipment and according to the foundation design plan. If any excavation is necessary within the area to be occupied by bearing piles, that excavation should be completed before driving the piles. Also, a small starter hole may be hand dug at each pile location to receive the distal end of the first pile segment.

Additionally, prior to installation of the PGD piles, the piles or pile segments should be stored a suitable distance from the construction activity to prevent incidental damage to the equipment, the piles, and any persons. To optimize the structural integrity of the foundation, the piles should be free of damage before being installed. It is preferred that the PGD piles used are made by or for American Piledriving Equipment, Inc. which are made of steel casing pipe segments in 5 to 40 foot lengths with diameters of 4.5 inches, 5.5 inches, 7 inches, 9.625 inches, 11.75 inches and 13.375 inches and comply with ASTM A328/A328M-07 standards for deep foundation systems, although it should be understood that other suitable PGD piles may be used.

Before installation, each pile should be made ready for installation and carefully transported to the installation location. The PGD piles of American Piledriving Equipment, Inc. have protective plastic caps on each end of the pile shaft segment. Such protective plastic caps should not be removed until moved into driving position. The starter pile segment has a socket end with threads, a drive tip end, helical blades, and at least one grout port. Other pile shaft segments each have a socket end and a drive end and each end has threads. To connect the pile segments together, a drivable coupler is used.

A drivable coupler is either pre-attached to the socket end of starter pile segment or may be manually attached to the socket end of the starter pile segment. With a safety chain inserted, the drivable coupler at the socket end of the starter pile segment may be manually set into a pile drill head that has a grout line attachment. The pile drill head may be suspended from an appropriately sized excavator for open site conditions or from the low-overhead equipment (e.g., a skid-steer) for use under low ceiling conditions. The starter pile segment may then be moved into place over the marked location and lowered into place.

Once it is determined that the starter pile segment is in the proper location and orientation and the surroundings are clear the starter pile segment may be drilled down until the remaining shaft portion of the segment is approximately one foot above grade. The drill socket may then be disconnected from the starter pile segment.

The next pile shaft segment may then be transported into position using the same procedure as described above for the starter pile segment. Once the next pile shaft segment is in position, a laborer manually aligns the drive end of the next pile shaft segment with the threads of the starter pile segment and turns the next pile segment until its threads catch enough with the threads of the installed starter pile segment. After the next pile segment is inserted and deemed within the thread, a drivable coupler is threaded onto the socket end of the next pile segment and the pile drill head engages the drivable coupler to drill the next pile shaft segment into the portion of the starter pile segment that remained above grade. This causes the next pile shaft segment to catch into the starter pile segment and irreversibly locks both segments together. A grout plug may then be inserted into the socket end of the pile shaft segment so that simultaneously with the drilling, grout may be pumped under pressure into the interior of the pile segments to fill the interior and exit out the one or more grout ports. As the pile segments are drilled down, grout encases the pile segments in a mixture of the grout and the soil disturbed by the helical blades of the starter pile along the entire borehole.

In a similar manner, subsequent pile shaft segments are added to the pile and encased in grout until the pile toe reaches the depth specified by engineering for the pile depth. Typically, the last pile shaft segment is driven to a depth that has about three feet above grade, with its shaft being grout filled to approximately one inch below the threaded coupler section. Also, all grout, if any, should be removed from the threads. This height is desirable for on-site dynamic load testing of the pile, and if each pile is driven to this height and grout filled as mentioned then each pipe pile may be dynamic load tested. The grout within the pile and encasing the pile is allowed to cure. Additionally, during pile installation, cylindrical grout samples are collected, cured and compressive strength-tested at 7, 10, and 28 days post-collection in accordance with ASTM C39/C39M.

In the interest of brevity, the nature of PGD pile components and the driving of the PGD piles are described here in a summary format. However, a more detailed description of this aspect of the invention is disclosed in the patent applications of American Piledriving Equipment, Inc. and published as United States Patent Application Publication Nos. US2013/0272799 and US2014/0056652 (herein sometimes referred to as the "APE applications"). These published APE applications and each of the published patents and patent applications to which these APE applications claim priority are hereby incorporated in their entirety into this application by this reference, and as if fully set forth herein. Again, it should be understood that PGD piles other than those described in these published applications may be used without departing from the scope and spirit of this invention.

Each piling should be drilled in this manner to ensure: 1) proper interlocking of each pile shaft segment, and 2) that the grout-soil mixture is evenly distributed along the entire borehole, totally encasing the below grade piling surface. Each pile should be driven continuously and without interruption to the specified depth or until the specified bearing capacity is obtained so that the concrete grout does not cure during installation.

If the installed pile is to be dynamically load tested, the pile may be prepared for such testing and the grout is allowed to cure. Because such dynamic load testing leaves the pile in a condition suitable for use, may be conducted under low ceiling conditions, and is considerably less expensive and less time-consuming to perform, such dynamic load testing may be performed on up to all of the installed piles that comprise the deep foundation for an elevated home or building.

Dynamic load testing is conducted to determine bearing capacity, dynamic pile tensile and compressive stresses (both axial and averaged over the pile cross section), pile integrity, and hammer performance parameters. These and other possible determinations resulting from dynamic load testing may be helpful in establishing compliance with flood insurance mandated requirements and other engineering requirements, as well as simple peace of mind for the owner of the building supported by dynamically load tested piles.

If the installed pile is not to be tested or after dynamic load testing has been completed on the pile, a pile cap connector may be inserted onto the top of the installed pile. The pile cap connector may have a pile cap having one of several configurations and serves to connect the pile to a support beam or girder for house or building. Some pile cap connectors may be configured to accept the run of the support beam or girder while others may be configured to accept the end of a support beam or girder. Still other pile cap connectors may have height adjustability. The manner in which exemplary pile cap connectors may be height adjustable is disclosed in detail in the applicant's patent application titled "Pile Cap Connectors" filed concurrently with this application. The disclosure of the concurrently filed application (U.S. patent application Ser. No. 14/289,595, filed May 28, 2014) is hereby incorporated in its entirety into this application by this reference, and as if fully set forth herein.

Once a pile cap connector is set to design height and secured to each pile, the support beams or girders may be secured to the various pile cap connectors. In situations where the array of pipe piles forming the deep pile foundation involve an elevated home or building, the home or building may then be lowered onto and secured to the support beams or girders to create a strong, continuous load path between the house and the ground.

These and other features of the method of the present invention will become more fully apparent from the following description, or may be learned by the practice of the invention as set forth hereinafter.

BRIEF DESCRIPTION OF THE SEVERAL VIEWS OF THE DRAWINGS

In order that the manner in which the above-recited and other features and advantages are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 2 is an exploded plan view of an exemplary starter pile segment and a drive coupler;

FIG. 3 is a plan view of the starter pile segment of FIG. 2 with the drive coupler attached;

FIGS. 10A-10C are a series of views of an exemplary pile cap wherein FIG. 10A is an exploded, perspective view of the pile cap showing its individual component parts, FIG. 10B is an elevation side view of the pile cap as assembled, and FIG. 10C is an elevation side view of the pile cap showing the disposition of a girder or beam upon the alternative pile cap;

FIGS. 11A-11C are a series of views of an exemplary, alternative pile cap wherein FIG. 11A is an exploded, elevation side view of the alternative pile cap showing its individual component parts, FIG. 11B is a top plan view of the alternative pile cap as assembled, and FIG. 11C is an elevation side view of the alternative pile cap showing the disposition of a girder or beam upon the alternative pile cap;

FIGS. 12A-12C are a series of views of another exemplary, alternative pile cap wherein FIG. 12A is an exploded, elevation side view of the alternative pile cap showing its individual component parts, FIG. 12B is a top plan view of the alternative pile cap as assembled, and FIG. 12C is an elevation side view of the alternative pile cap showing the disposition of a girder or beam upon the alternative pile cap;

DETAILED DESCRIPTION OF THE INVENTION

Figure 1:
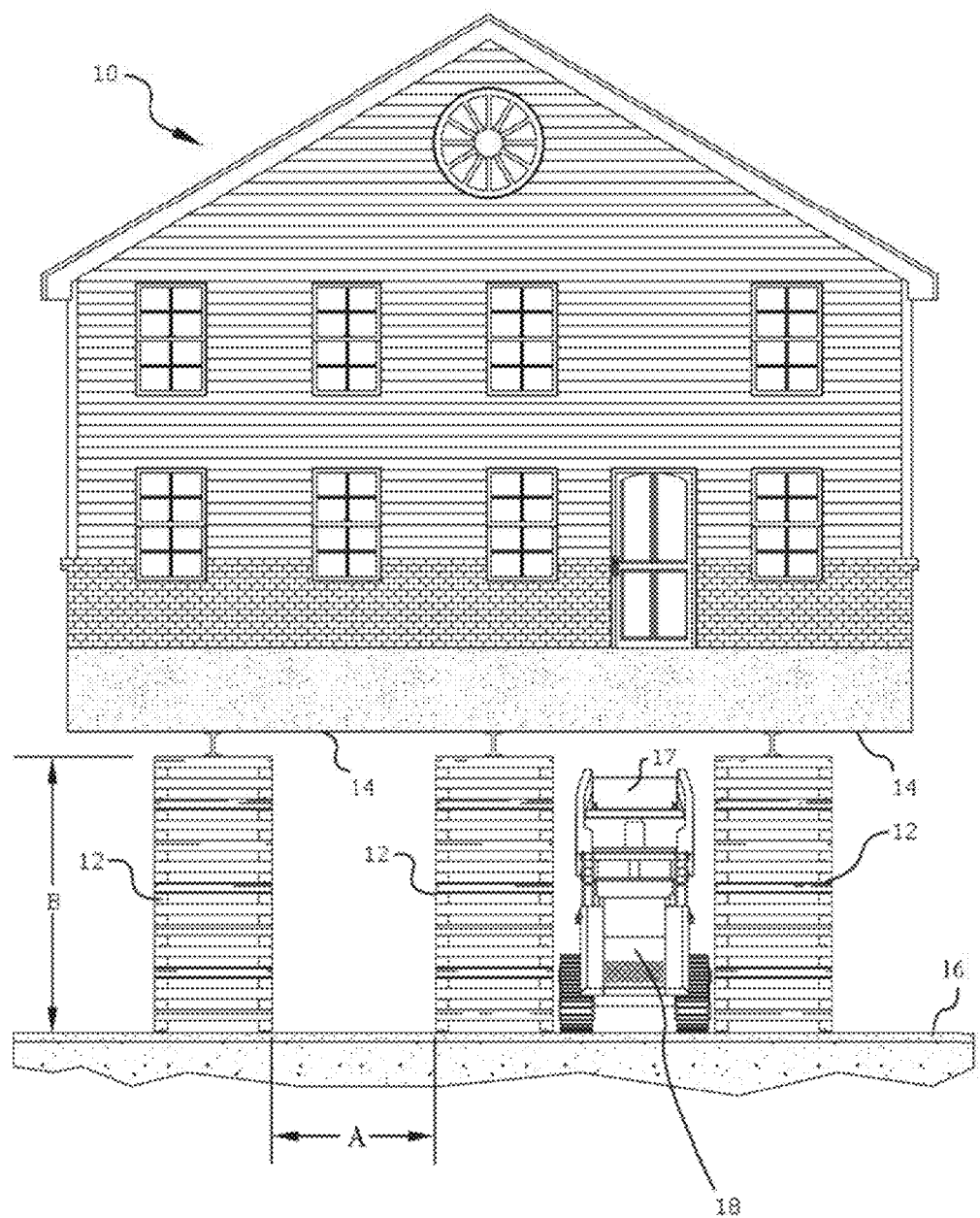
FIG. 1 is an elevation view of a home that has been lifted onto support cribbing and showing how low-overhead equipment may maneuver underneath the lifted home.

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the present invention, as represented in the figures, is not intended to limit the scope of the invention, as claimed, but is merely representative of presently preferred embodiments of the invention.

The word "exemplary" is used exclusively herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

In this application, the phrases "connected to", "coupled to", and "in communication with" refer to any form of interaction between two or more entities, including mechanical, capillary, electrical, magnetic, electromagnetic, pneumatic, hydraulic, fluidic, and thermal interactions.

The phrases "attached to", "secured to", and "mounted to" refer to a form of mechanical coupling that restricts relative translation or rotation between the attached, secured, or mounted objects, respectively. The phrase "slidably attached to" refer to a form of mechanical coupling that permits relative translation, respectively, while restricting other relative motions. The phrase "attached directly to" refers to a form of securement in which the secured items are in direct contact and retained in that state of securement.

The term "abutting" refers to items that are in direct physical contact with each other, although the items may not be attached together. The term "grip" refers to items that are in direct physical contact with one of the items firmly holding the other. The term "integrally formed" refers to a body that is manufactured as a single piece, without requiring the assembly of constituent elements. Multiple elements may be integrally formed with each other, when attached directly to each other from a single work piece. Thus, elements that are "coupled to" each other may be formed together as a single piece.

The exemplary methods of the present invention relate to dynamic load testing pipe piles forming deep pile foundations constructed for existing residential homes and other buildings more efficiently, in less time, and cost-effectively. Although the methodolgy of the present invention is particularly suitable for existing homes or buildings, the methodology is equally suitable for providing deep pile foundations for homes and other buildings under construction. For purposes of this application the term "building" includes all types of buildings, including but not limited to residential homes, commercial buildings, outbuildings, garages, cottages, sheds, boat houses, and any other type of building that would justify having a deep pile foundation.

The methodology involves furnishing and installing pressure grouted displacement piles ("PGD piles") that may be dynamically load tested and capping the PGD piles under low ceiling or open site conditions. Further, the PGD piles may be placed at locations as approved on engineering drawings. The methods of the present invention are particularly suitable for dynamic load testing retrofitted elevated foundations for homes or other buildings that must be lifted and placed onto elevated foundations in order to qualify for NFIP coverage. However, with slight modification, a person of ordinary skill in the art can also implement the principles of the invention for use with open site construction as well.

The known conventional, industry standard process for lifting a residential home and placing it onto an elevated concrete block or helical micropile foundation, with a two-to-six foot deep concrete grade berm, takes approximately 28 days to complete, is costly, and has limited foundational integrity. On the other hand, the methods of the present invention reduce the cycle time needed to lift and anchor a residential home or other building onto a deep pile foundation that may be dynamically loaded tested to approximately 7 to 10 days, depending on the grout cure time needed. Also, the dynamically load tested deep pile foundation provided is a sturdier, more durable foundation than foundations created using conventional methods.

Prior to installation of the PGD piles, the site should be made ready for installation. For an existing home or building, the utilities are disconnected and the home or building is lifted onto stable stacks of wood cribbing using standard industry practices so that the lowest part of the home or building is approximately 10 to 12 feet above grade. The cribbing should be spaced so that low-overhead equipment (e.g., a skid steer or a post driver) may maneuver between the cribbing stacks. Typically, a distance of 80 to 90 inches will be sufficient distance between cribbing stacks to allow low-overhead equipment to maneuver under the base of the elevated home or building. However, a predetermined distance of less than 80 inches may be suitable if the low-overhead equipment is more narrow than typical or exhibits superior maneuverability in tight space. Since dislodging a cribbing stack may be catastrophic, it is better to err on the side of a larger predetermined distance than to test the bounds of a narrower distance. The appropriate predetermined distance between cribbing stacks will likely be determined by engineering requirements for the particular home or building.

FIG. 1 illustrates a building 10 that has been lifted onto spaced cribbing stacks 12 so that the underside 14 of the building is elevated to a predetermined elevation A above grade 16. This predetermined elevation A is greater than the height of low-overhead equipment 18 during use. The cribbing stacks 12 should be spaced apart a predetermined distance B so that low-overhead equipment 18, such as a skid steer or a post driver, with whatever attachments needed, such as a drill 17 with a pile drill head 19 or a drop hammer 142 (see FIG. 20), may maneuver between the cribbing stacks 12, while maintaining a sturdy and reliable, temporary foundation for the elevated building 10.

To understand the likely pile driving conditions and how the soil may interact with the PGD piles, one or more soil borings should be performed to a depth specified by the engineer on the site so that the engineer may determine the specific locations for each of the PGD piles needed to support the existing home or building 10 or the home or building under construction. Also, any existing foundation should be demolished and removed so that the site may be cleared of all construction debris and the ground surface may be leveled and worked to support low-overhead equipment 18.

The locations for the piles, as determined by the engineer on the site, may be identified by measurement and may be paint-marked on suitable grade 16 as determined by proper surveying equipment and according to the foundation design plan. If any excavation is necessary within the area to be occupied by bearing piles, that excavation should be completed before driving the piles. Also, a small starter hole may be hand dug at each pile location to receive the drive end of the first pile segment.

Additionally, prior to installation of the PGD piles, the piles or pile segments should be stored a suitable distance from the construction activity to prevent incidental damage to the equipment, the piles, and any persons. To optimize the structural integrity of the foundation, the piles should be free of damage before being installed. It is preferred that the PGD piles used are made by or for American Piledriving Equipment, Inc. which are made of steel casing pipe segments in 5 to 40 foot lengths with diameters of 4.5 inches, 5.5 inches, 7 inches, 9.625 inches, 11.75 inches, and 13.375 inches and comply with ASTM A328/A328M-07 standards for deep foundation systems, although it should be understood that other suitable PGD piles may be used. Of course, for pipe piles installed beneath an elevated home or building 10, steel casing pipe segments of 5 foot length are particularly suitable; however, if a building 10 is elevated 12 feet or more, slightly longer segments may be used. Segments that are longer than the elevated height A of the building 10 may only be used in open site constructions.

FIG. 2 shows an exploded view of a pile segment 20 and a drivable coupler 22 that serves as a component part of a pipe pile 24 (including, but not limited to, a PGD pile when installed with grouting and bearing the same reference number 24). The pile segment 20 shown is a starter pile segment 26.

Figures 5, 6:
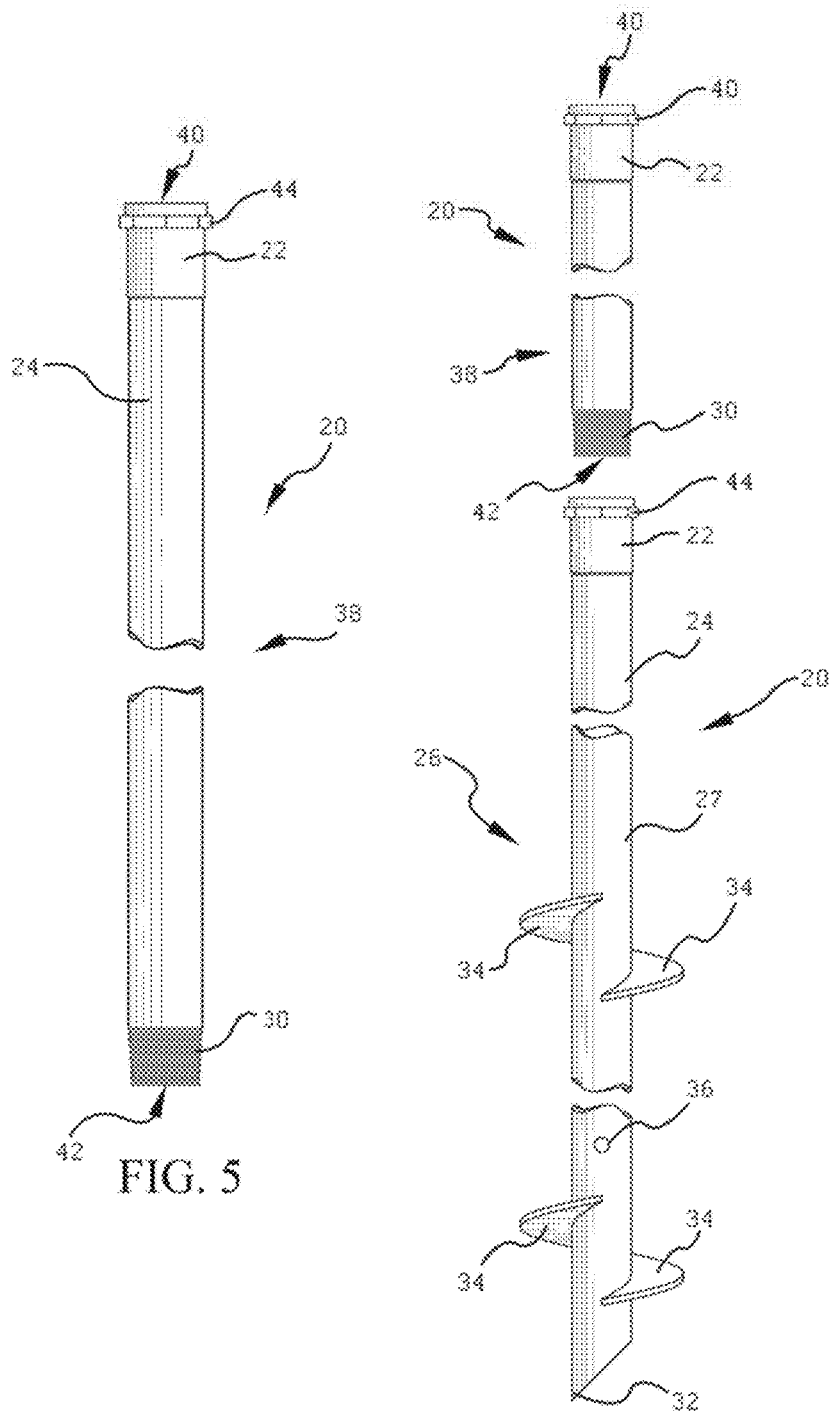
FIG. 5 is a plan view of a pile shaft segment with an exemplary pre-attached drive coupler.
FIG. 6 is an exploded plan view of an exemplary starter pile segment with a pre-attached drive coupler and a pile shaft segment positioned for insertion and connection.

Before installation, each pile segment 20 should be made ready for installation and carefully transported to the installation location. The PGD piles 24 of American Piledriving Equipment, Inc. have protective plastic caps (not shown) on the threaded ends of each pile segment 20. Such protective plastic caps should not be removed until moved into driving position. The starter pile segment 26 has a shaft portion 27, a socket end 28 with threads 30, a drive tip end 32, helical blades 34, and at least one grout port 36. Other pile shaft segments 38 (as shown in FIGS. 5 and 6) each have a socket end 40 and a drive end 42 and each end has threads 30. To connect the pile segments 20 together, the drivable coupler 22 is used.

Figure 4:
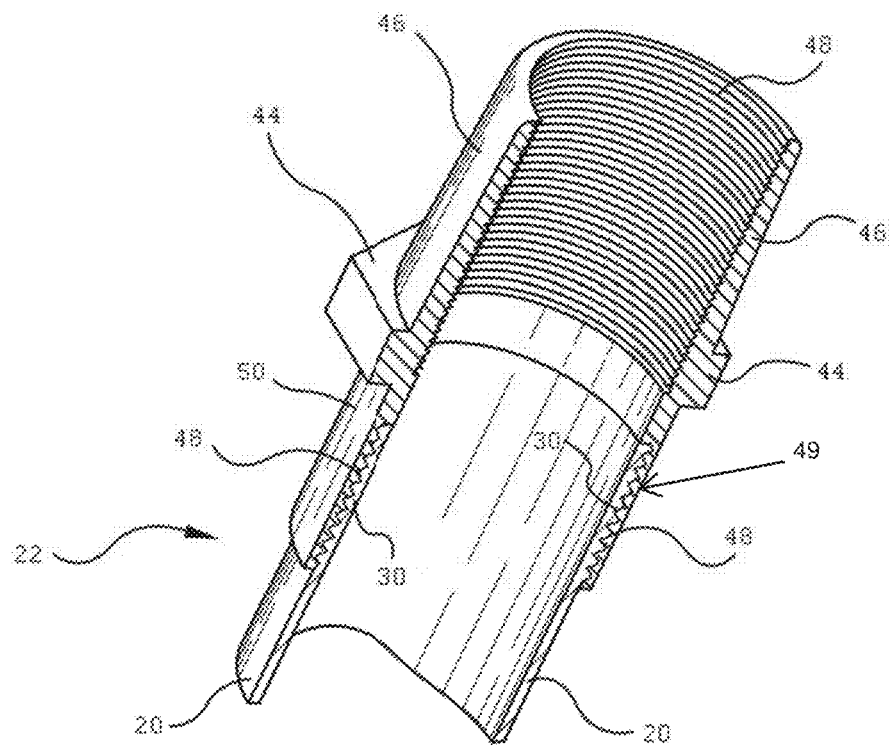
FIG. 4 is a perspective, sectional view of an exemplary drive coupler.

As shown in FIGS. 2 and 3, the drivable coupler 22 is either pre-attached to the socket end 28 of starter pile segment 26 or may be manually attached to the socket end 28 of the starter pile segment 26. An exemplary drivable coupler 22, as shown in FIG. 4, has a socket receiving, polygonal drive ring 44 (typically hexagonal or octagonal), an upper sleeve portion 46 with internal threads 48 for receiving threads 30 at the drive end 42 of a pile segment 20, and a lower sleeve portion 50 with an internal interface 49 for receiving the socket end 28, 40 of a pile segment 20. The internal interface 49 may be threads 48 for engaging threads 30 in the socket end 28, it may be a smooth wall (not shown) wherein the connection of the drivable coupler 22 to the pile segment 20 is by welding, adhesive, or any other suitable securement, or any other securement that connects the drivable coupler 22 to the pile segment 20.

With a safety chain inserted, the drivable coupler 26 at the socket end 28 of the starter pile segment 26 may be manually set into a pile drill head 19 that has a grout line attachment (not shown in this application in the interest of brevity, but described and illustrated in the APE applications expressly incorporated herein by reference). The pile drill head 19 may be suspended from an appropriately sized excavator for open site conditions or from low-overhead equipment 18, such as a skid-steer with a drill 17 attachment, for use under low-overhead conditions. The starter pile segment 26 may then be moved into place over the marked location and lowered into place.

Once it is determined that the starter pile segment 26 is in the proper location and orientation and the surroundings are clear, the starter pile segment 26 may be drilled down until the shaft portion 27 of the starter pile segment 26 is approximately one foot above grade 16. The pipe drill head 19 (which may include a socket to engage and drive the drive ring 44) may then be disconnected from the starter pile segment 26 so that the starter pile segment 26 may receive the threaded end of the next pile segment 20.

FIG. 5 shows a pile segment 20 of the pile shaft segment 38 type, with a drivable coupler attached to its socket end 40, and FIG. 6 is an exploded view of a pile shaft segment 38 aligned and ready for insertion into the starter pile segment 26. Successive pile segments 20 may be added to form the pipe pile 24, which is an aggregate of linearly connected pile segments 20, until the pipe pile 24 has the desired length to create a component of the deep pile foundation.

Figure 7:
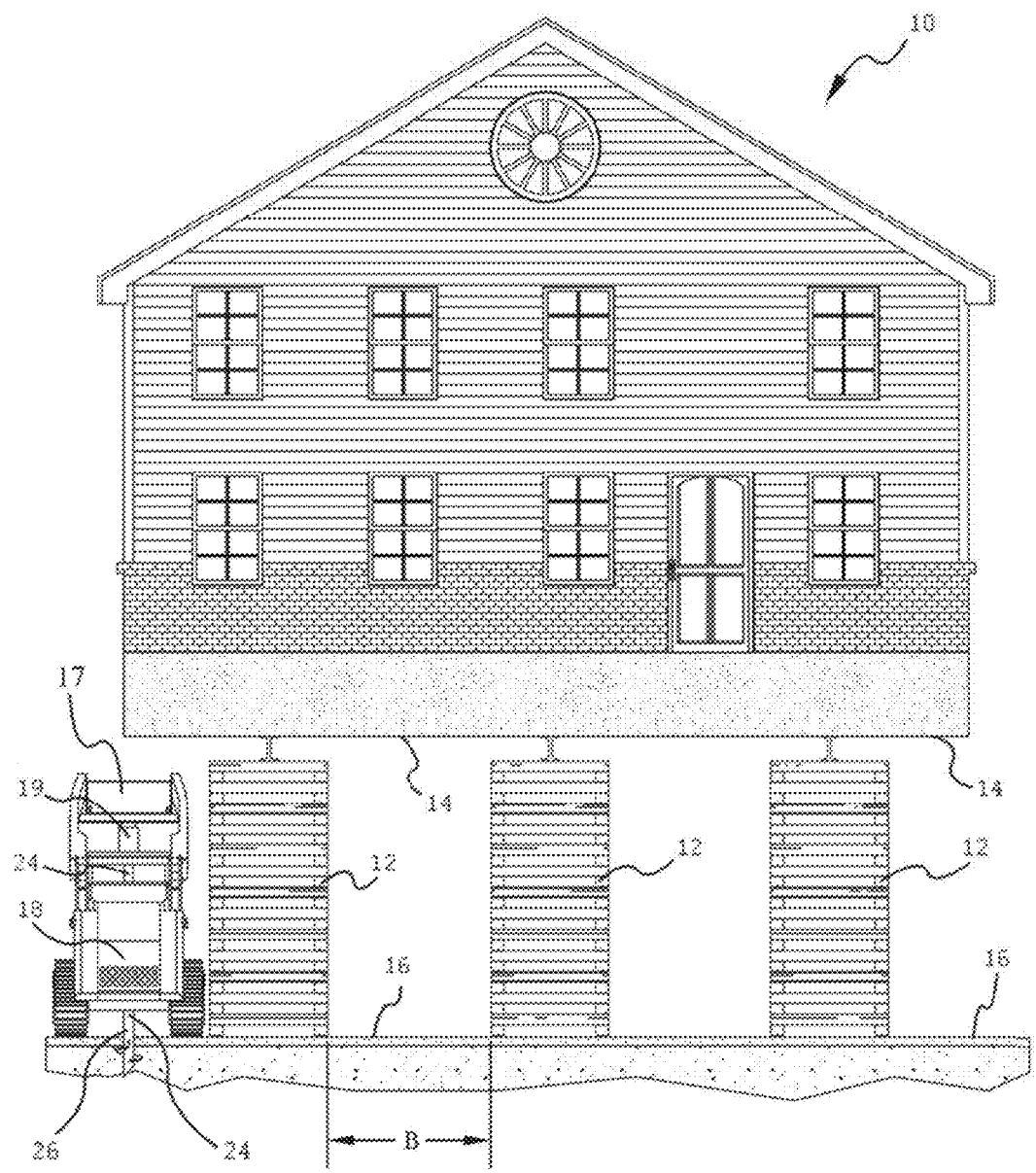
FIG. 7 is an elevation view of the home of FIG. 1 that has been lifted onto support cribbing and showing a piece of low-overhead equipment in position to drive a corner pipe piling.

Turning now to FIG. 7, an elevation view of the building 10 of FIG. 1 is shown with exemplary low-overhead equipment 18 with a drill 17 attachment positioned to drive a corner pipe pile 24. In some exemplary embodiments of the present invention, it may be advantageous to drive the corner pipe piles 24 before driving the interior pipe piles 24. First, if a mishap occurs with the cribbing stacks 12 while maneuvering the low-overhead equipment 18 between and around the cribbing stacks 12, at least a rudimentary balanced foundation will be in place at the corners of the building 10 to support the building 10 for a few moments, to allow the workmen that may be beneath the building 10 to escape before a cribbing stack 12 and/or the building 10 collapses. And second, the corner pipe piles 24 will not render any of the other locations for pipe piles 24 inaccessible. However, it should be understood that the pipe piles 24 may be driven in any order that will not render any of the locations for pipe piles 24 inaccessible.

Figure 8:
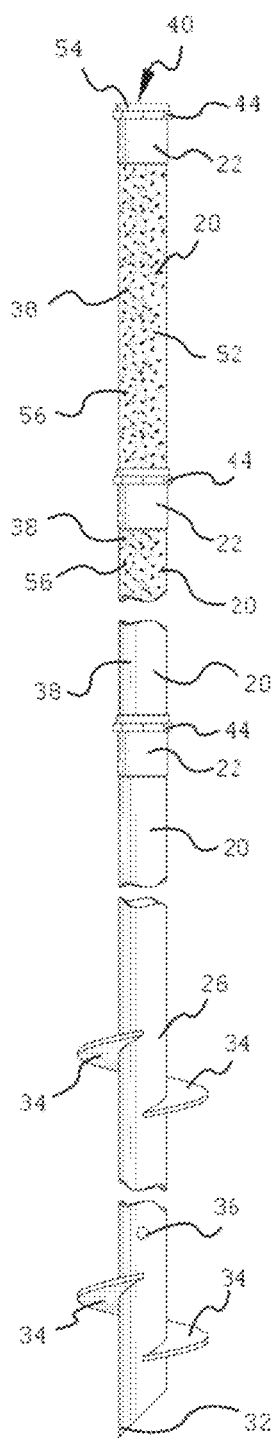
FIG. 8 is a plan view of an exemplary pipe pile assembly showing an exemplary epoxy coating over an upper portion of the pipe pile assembly.
Figure 9:
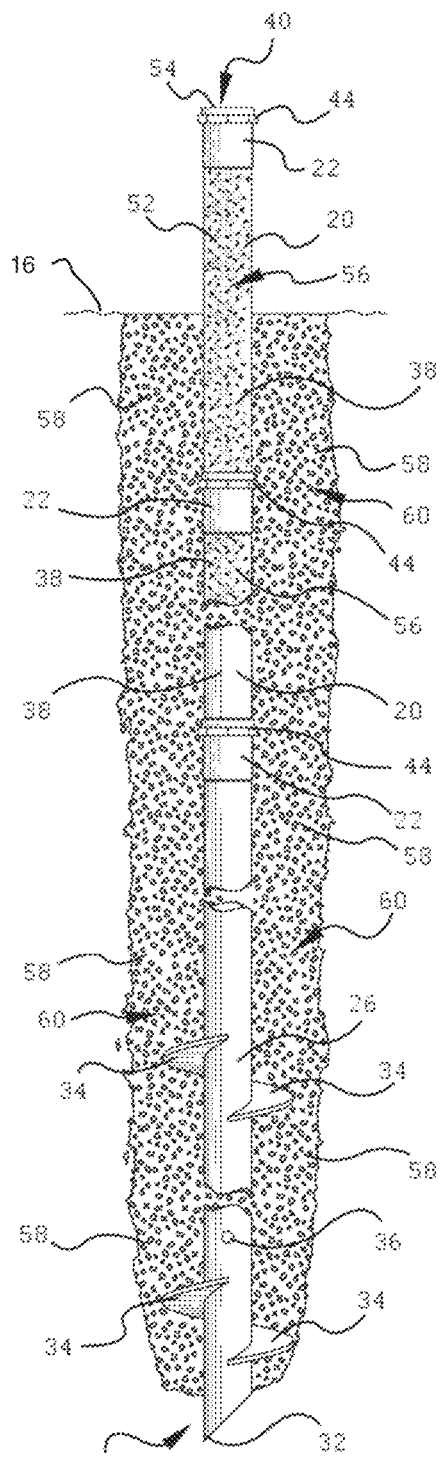
FIG. 9 is an elevation section view showing the exemplary pipe pile assembly of FIG. 8 as driven into the soil and illustrating the grout-soil mixture encasing the pipe pile assembly resulting from pressure grouting during the driving of the pipe pile assembly, and showing a portion of the pipe pile assembly exposed above grade.

FIGS. 8 and 9 show that once the starter pile segment 26 has been driven, the next pile segment 20, a pile shaft segment 38, may then be transported into position using the same procedure as described above for the starter pile segment 26. Once the pile shaft segment 38 is in position, a laborer may manually align the drive end 42 of the pile shaft segment 38 with the internal threads 48 of the drivable coupler 22 as attached to the starter pile segment 26. The laborer may then threadably turn the pile segment 38 until its threads 30 catch enough with the internal interface 49 of the drivable coupler 22, thereby connecting the pile shaft segment 38 to the starter pile segment 26. After the pile shaft segment 26 is inserted and deemed fully-seated in threaded engagement and secured (by threads, welding, an adhesive, or any other suitable securement), another drivable coupler 22 may be secured onto the socket end 40 of the pile shaft segment 38. The pile drill head 19 is then directed to engage the drive ring 44 of this drivable coupler 22 to enable the drill down of the pile shaft segment 38. This causes the pile shaft segment 38 to catch into the drivable coupler 22 attached to the starter pile segment 26 and irreversibly locks both segments 20 together.

In a similar manner, subsequent pile segments 20 may be added to the string of pile segments 20 comprising the pipe pile 24, until the desired length for the pipe pile 24 is achieved. Each pipe pile 24 comprises a starter pile segment 26 and an uppermost pile segment 52 and any number of pile shaft segments 38 intermediate thereof, spanning from drive tip end 32 to a top end 54 of the uppermost pile segment 52. FIG. 8 illustrates an exemplary pipe pile 24 as an assembly of pile segments 20 with at least one pile shaft segment 38 disposed between a starter pile segment 26 and an uppermost pile segment 52. In some exemplary embodiments of the pipe pile 24, at least a portion of the pipe pile 24 is covered with an epoxy coating 56. For example, an epoxy paint coating 56 may be applied to the pile segments 20 that will extend above grade 16 and may also be applied to the pile segments that extend below grade 16 for a predetermined distance below grade 16.

Before the combination of the starter pile segment 26 and the first pile shaft segment 38 is drilled down, a grout plug (not shown, see the APE applications for exemplary grout plugs and other grout delivery components) may then be inserted into the socket end 40 of the pile shaft segment 38. This will enable the delivery of grout 58 simultaneously with the drilling. With the grout plug in place and the pile drill head 19 engaging the uppermost drive ring 44, grout 58 may be pumped under pressure into the interior of the pile segments 20 to fill the interior (see FIG. 17) and exit out the one or more grout ports 36. As each successive pile segment 20 is drilled down, with grout being pumped in continuously during drilling, grout encases the pipe pile 24 in a mixture 60 of the grout and the soil disturbed by the helical blades of the starter pile segment 26 along the entire borehole.

In a similar manner, each subsequent pile shaft segment 38 is added to the pipe pile 24 and encased in the grout-soil mixture 60 until the pile toe 62 reaches the depth specified by engineering for the pile depth, as shown in FIG. 9. Typically, the last pile shaft segment 38, herein referred to specifically as the uppermost pile shaft segment 52, is driven to a depth so that the top end 54 of the uppermost pile shaft segment 52 and the PGD pile 24 is about three feet above grade 16. This height is desirable for on-site dynamic load testing of the PGD pile 24. Before on-site dynamic load testing, the grout 58 within the PGD pile 24 and the grout-soil mixture 60 encasing the PGD pile 24 is allowed to cure. Additionally, during pile installation, cylindrical grout samples are collected, cured and compressive strength-tested at 7, 10, and 28 days post-collection in accordance with ASTM C39/C39M.

Where acceptable, a quick-curing grout 58 may be used to assist with reducing the overall time to construct the deep pile foundation.

As mentioned above, for brevity, the nature of PGD pile 24 components and the driving of the PGD piles 24 are described herein in a summary format. However, a more detailed description of this aspect of the invention is disclosed in the APE applications. Again, it should be understood that PGD piles other than those described in these published applications may be used without departing from the scope and spirit of this invention. For example, in some situations such as to elevated smaller buildings, pipe piles 24 without pressure grouting may be suitable to use.

Each PGD pile 24 should be drilled in this manner to ensure: 1) proper interlocking of each pile shaft segment 38, and 2) that the grout-soil mixture 60 is evenly distributed along almost all of the subterranean portion of the PGD pile 24, encasing the below-grade 16 PGD pile 24 surface. Each PGD pile 24 should be driven continuously and without interruption to the specified depth or until the specified bearing capacity is obtained so that the concrete grout 58 does not cure during installation.

If the installed PGD pile 24 is to be dynamically load tested, the PGD pile 24 may be prepared for such testing and the grout 58 and grout-soil mixture 60 are allowed to cure. Because such dynamic load testing leaves the PGD pile 24 in a condition suitable for use eliminating the need for pilot piles, may be conducted under low overhead conditions, and is considerably less expensive and less time-consuming to perform, such dynamic load testing may be performed on any of the installed PGD piles 24 and even all of the installed PGD piles 24 that comprise the deep pile foundation for an elevated home or building 10. By testing all of the installed PGD piles 24, the load capacity of the deep pile foundation may be determined with more certainty than heretofore was available.

Dynamic load testing may be conducted to determine bearing capacity, dynamic pile tensile and compressive stresses (both axial and averaged over the pipe pile 24 cross section), pile integrity, and hammer performance parameters. These and other possible determinations resulting from dynamic load testing may be helpful in establishing compliance with flood insurance mandated requirements and other engineering requirements, as well as simple peace of mind for the owner of the building 10 supported by dynamically load tested piles.

If the installed pipe pile 24 is not to be tested or after dynamic load testing has been performed on the pipe pile 24, a pile cap connector 63 may be inserted onto the top of the installed pipe pile 24. Each of the pile cap connectors 63 may be or include pile caps 64 having one of several configurations and each pile cap connector 63 serves to connect the pipe pile 24 to a support beam or girder 66 for supporting the house or building 10. FIGS. 10A-10C, 11A-11C, 12A-12C, 13 and 14 illustrate various exemplary pile cap connectors 63.

Figure 10B:
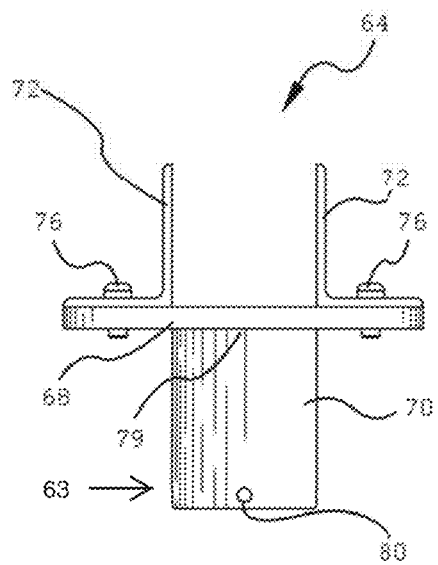
Figure 10C:
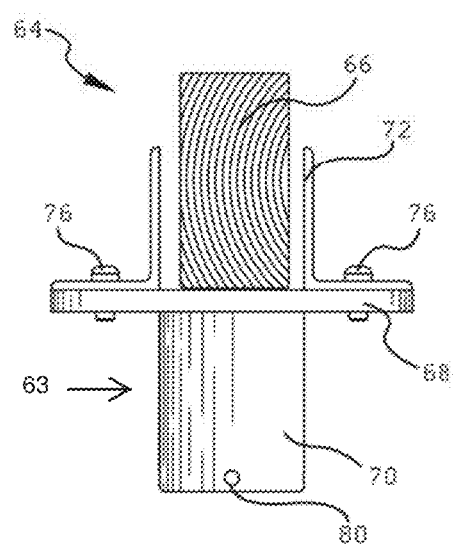
Figure 10A:
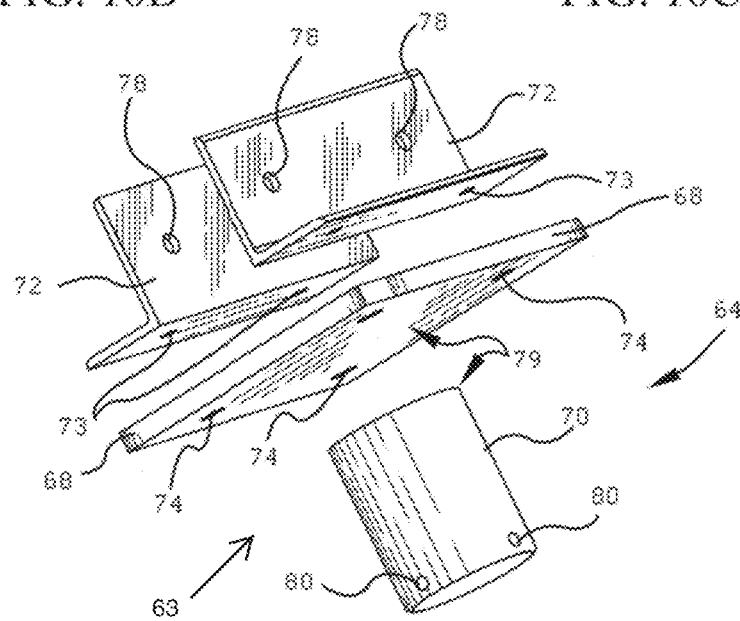
Figure 11C:
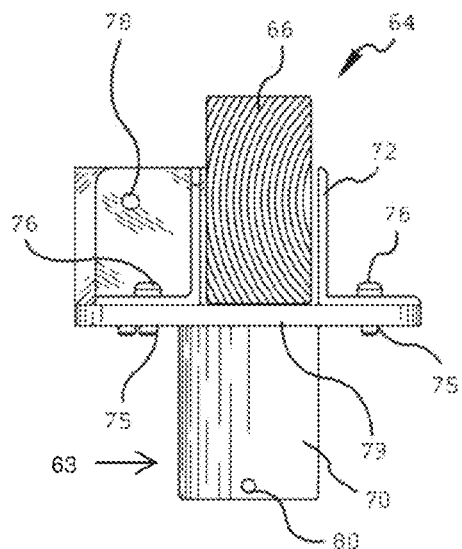
Figure 11B:
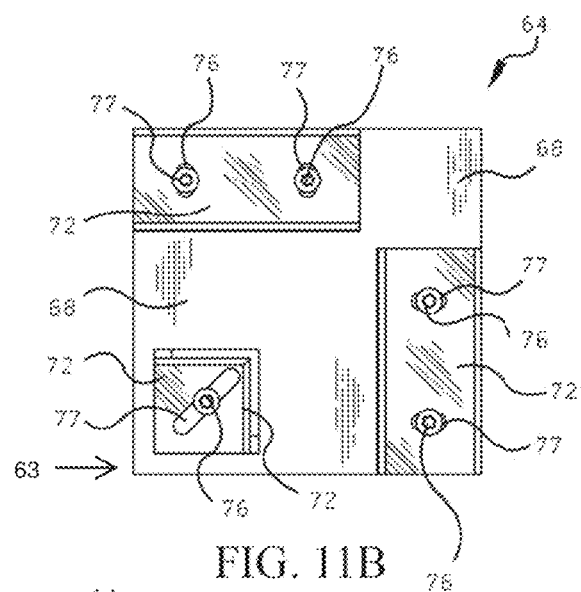
Figure 11A:
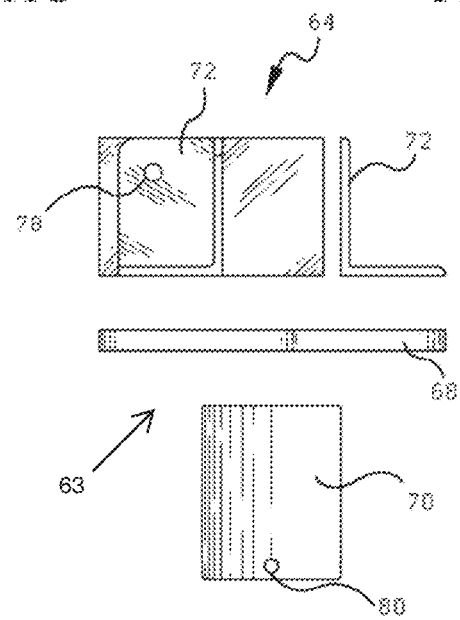

Some pile caps 64 may be configured to accept the run of the support beam or girder 66 (see FIGS. 10A-10C) while others may be configured to accept the end of a support beam or girder 66 (see FIGS. 11A-11C). FIGS. 10A-10C are a series of views of one exemplary pile cap connector 63 that is only a pile cap 64. FIG. 10A is an exploded, perspective view of the pile cap 64 showing its individual component parts, including a support plate 68, an outside sleeve 70, and a pair of angle braces 72. The support plate 68 has a plurality of bolt holes 75 that are elongate bolt holes 74 for receiving carriage bolts 76 to connect the angle braces 72 for slidable adjustment before securing the angle braces 72. The angle braces 72 have bolt holes 73 and anchor holes 78 through which bolts (not shown) may be passed to secure the pile cap 64 to the beam or girder 66. The outside sleeve 70 is welded (the weld location is designated by reference number 79) to the underside of the support plate 68, or may be secured to the underside in any suitable fashion that will maintain the integrity of the connection against the anticipated stresses and strains that may be encountered by the foundation. The outside sleeve 70 has an inside diameter that is slightly larger than the outside diameter of the top end 54 of the pipe pile 24 and a plurality of holes 80 for plug welding to secure the outside sleeve 70 to the uppermost pile segment 52 of the pipe pile 24. FIG. 10B is an elevation side view of the pile cap 64 as assembled with the angle braces 72 secured to the support plate 68 by carriage bolts 76 and the outside sleeve 70 secured to the underside of the support plate 68. FIG. 10C is another elevation side view of the pile cap 64 showing the disposition of a girder or beam 66 upon the exemplary pile cap 64.

Similarly, FIGS. 11A-11C are a series of views of an exemplary pile cap connector 63 in the form of an alternative pile cap 64 with angle braces 72. FIG. 11A is an exploded, elevation side view of the alternative pile cap 64 showing its individual component parts, including a support plate 68, an outside sleeve 70, and angle braces 72 having different configurations from those of FIGS. 10A-10C. The support plate 68 has a plurality of bolt holes 75 for receiving carriage bolts 76 to connect the angle braces 72. The angle braces 72 have elongate bolt holes 77 and anchor holes 78 through which bolts (not shown) may be passed to secure the pile cap 64 to the beam or girder 66. The elongate bolt holes 77 enable slidable adjustment before securing the angle braces 72 to the support plate 68. The outside sleeve 70 is welded (the weld location is designated by reference number 79) to the underside of the support plate 68, or may be secured to the underside in any suitable fashion that will maintain the integrity of the connection against the anticipated stresses and strains that may be encountered by the deep pile foundation. The outside sleeve 70 has an inside diameter that is slightly larger than the outside diameter of the top end 54 of the pipe pile 24 and a plurality of holes 80 for plug welding to secure the outside sleeve 70 to the uppermost pile segment 52 of pipe pile 24. FIG. 11B is a top plan view of the pile cap 64 as assembled with the angle braces 72 secured to the support plate 68 by carriage bolts 76 and showing an exemplary configuration of the angle braces 72. FIG. 11C is an elevation side view of the pile cap 64 showing the disposition of a girder or beam 66 upon the alternative pile cap 64.

FIGS. 12A-12C are a series of views of yet another exemplary pile cap connector 63 in the form of an alternative pile cap 64. FIG. 12A is an exploded, elevation side view of the alternative pile cap 64 showing its individual component parts, including a support plate 68, an outside sleeve 70, and angle braces 72 having different configurations from those of FIGS. 10A-10C and 11A-11C. The support plate 68 has a plurality of bolt holes 75 for receiving carriage bolts 76 to connect the angle braces 72. The angle braces 72 have elongate bolt holes 77 and anchor holes 78 through which bolts (not shown) may be passed to secure the pile cap 64 to the beam or girder 66. The elongate bolt holes 77 enable slidable adjustment before securing the angle braces 72 to the support plate 68. The outside sleeve 70 is welded (the weld location is designated by reference number 79) to the underside of the support plate 68, or may be secured to the underside in any suitable fashion that will maintain the integrity of the connection against the anticipated stresses and strains that may be encountered by the foundation. The outside sleeve 70 has an inside diameter that is slightly larger than the outside diameter of the top end 54 of pipe pile 24 and a plurality of holes 80 for plug welding to secure the outside sleeve 70 to the uppermost pile segment 52 of pipe pile 24. FIG. 12B is a top plan view of the pile cap 64 as assembled with the alternative angle braces 72 secured to the support plate 68 by carriage bolts 76 and showing an exemplary configuration of the angle braces 72. FIG. 12C is an elevation side view of the pile cap 64 showing the disposition of a girder or beam 66 upon the alternative pile cap 64.

Figures 13, 14:
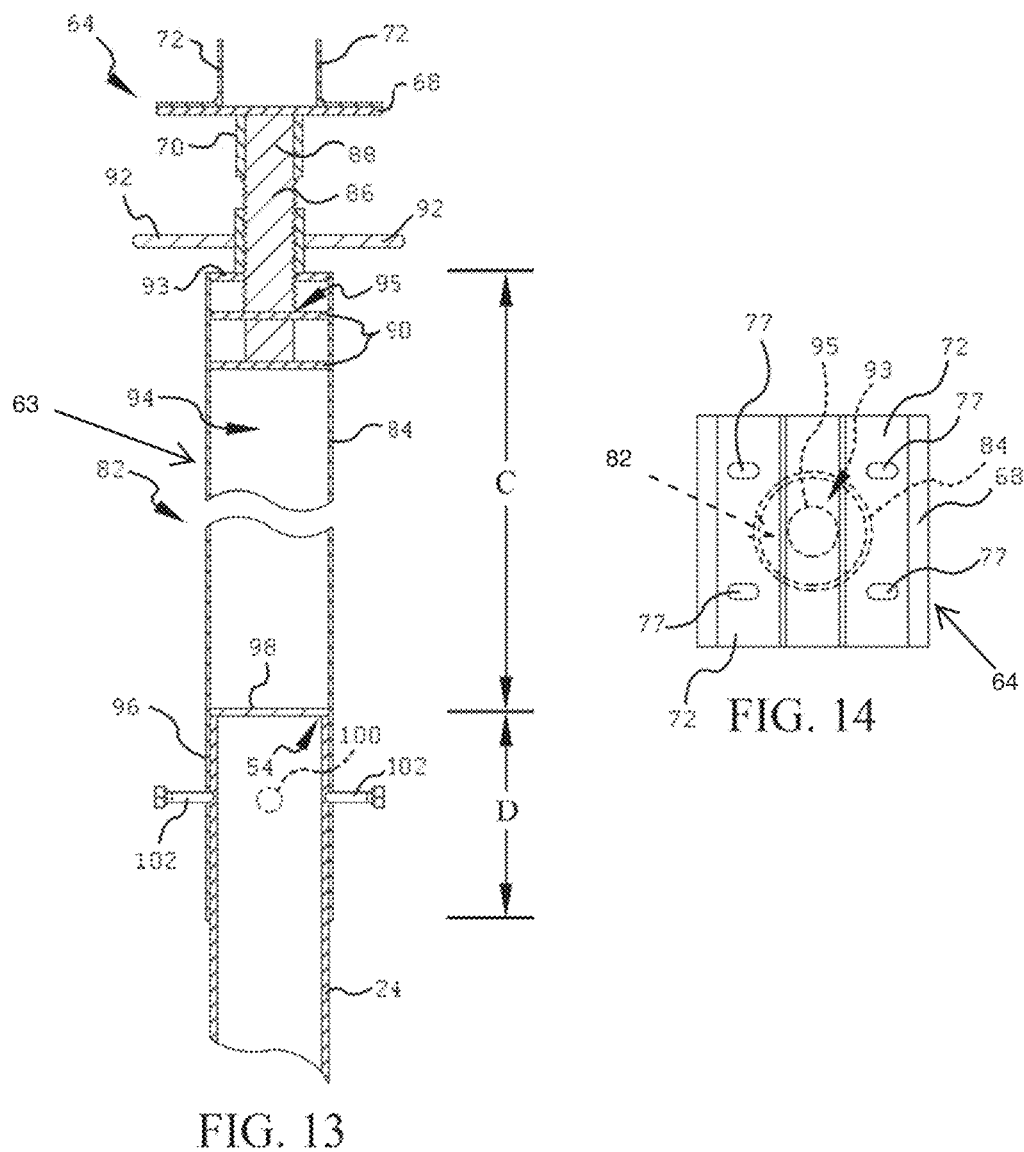
FIG. 13 is an elevation section view of an exemplary adjustable piling extension.
FIG. 14 is a top plan view of the adjustable piling extension with portions of the extension mechanism omitted so not to obscure other portions of the adjustable piling extension.

FIG. 13 is an elevation side view of an exemplary pile cap connector 63 with a pile cap 64 and an adjustable piling extension 82 used to span the distance from the top end 54 of the pipe pile 24 to the beam or girder 66. By way of example, the adjustable piling extension 82 of FIGS. 13 and 14 is just one way to span the distance from the top end 54 of the pipe pile 24 to the beam or girder 66, and is described herein as a representative example. For brevity, this one exemplary height-adjustable piling extension 82 will be described in detail. Other alternative adjustable piling extensions are contemplated and several alternative examples are disclosed in the concurrently filed application titled "Pile Cap Connectors" (U.S. patent application Ser. No. 14/289,595, filed May 28, 2014) incorporated in its entirety into this application by a previous reference herein, and as if fully set forth herein.

The adjustable piling extension 82 of FIGS. 13 and 14 has an extension shaft 84, a screw spindle 86 with a head 88 and at least one sliding support 90, and an adjusting nut 91 in the form of a handwheel nut 92. Atop the head 88 of the screw spindle 86, any one of a number of types of pile caps 64 (for examples, see FIGS. 10A-10C, 11A-11C, and 12A-12C) may be slipped on over the head 88 and/or may be secured to the head 88 via welding or any other suitable securement. Each sliding support 90 may be housed within a hollow portion 94 of the extension shaft 84 and may slide up or down as the handwheel nut 92 is rotated to adjust the overall length of the adjustable piling extension 82. The sliding supports 90 are secured to the screw spindle 86 such that the screw spindle 86 remains axially aligned during length adjustment.

The extension shaft 84 has an end plate 93 with a central bore 95 that allows the screw spindle 86 to pass therethrough and a hollow portion 94 that receives the sliding supports 90 for sliding engagement. The handwheel nut 92 abuts against the end plate 93. The extension shaft 84 also has a pile receiving end 96 that slips over the top end 54 of the pipe pile 24. In one embodiment, the top end 54 is prepared to receive the extension shaft 82 by securing a top end plate 98 to the top end 54 of the pipe pile 24. The pile receiving end 96 may also have set bolt holes 100 for receiving set bolts 102 to removably secure the extension shaft 84 to the pipe pile 24. Of course, it should also be understood that the extension shaft 84 may be more permanently secured to the pipe pile 24 by welding or any other suitable means.

The adjustable piling extension 82 may be made to various lengths C to reduce the need for an overly long screw spindle 86 and to accommodate the entire pipe pile assembly spanning the full distance of predetermined elevation A (see FIG. 1) without excessive adjustment. Also, pile receiving end 96 has a height D to assure that the slide-over connection with pipe pile 24 is stable and sturdy. It should be understood that the optimum height D may be a function of engineering design and length C.

FIG. 14 is a top plan view of the pile cap 64 showing the adjustable piling extension 82 in phantom lines with portions of the extension mechanism omitted so not to obscure other portions of the adjustable piling extension 82. In particular, the end plate 93 is annular with the central bore 95 and the inside and outside walls of the extension shaft 84 shown in phantom lines. Of course, the central bore 95 could have threads to receive the screw spindle 86 in threaded engagement, or it could have a bore diameter that will readily allow the screw spindle 86 to pass therethrough.

Figure 15:
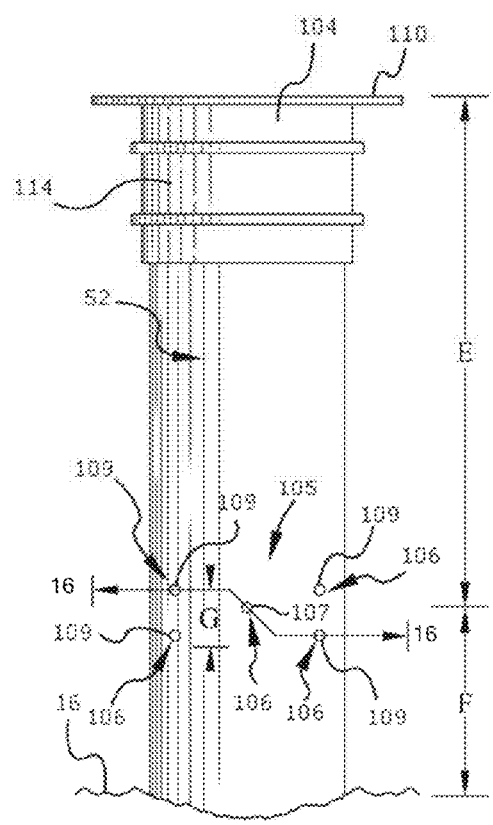
FIG. 15 is an elevation side view of an exemplary pipe piling with a test cap as disposed above grade and showing an exemplary sensor bore pattern.
Figure 16:
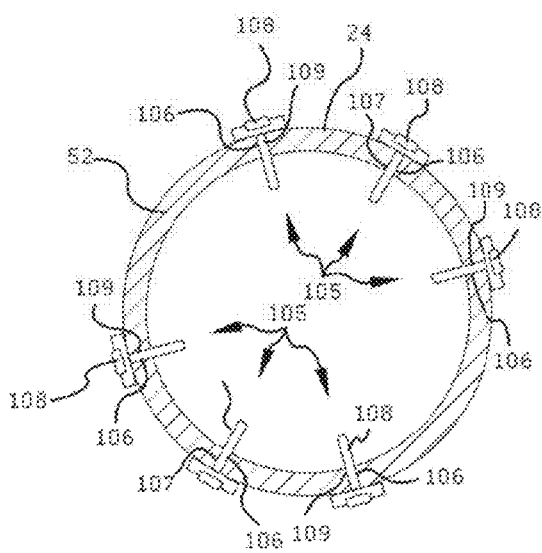
FIG. 16 is a sectional view of the pipe piling along line 16-16 of FIG. 15.
Figure 17:
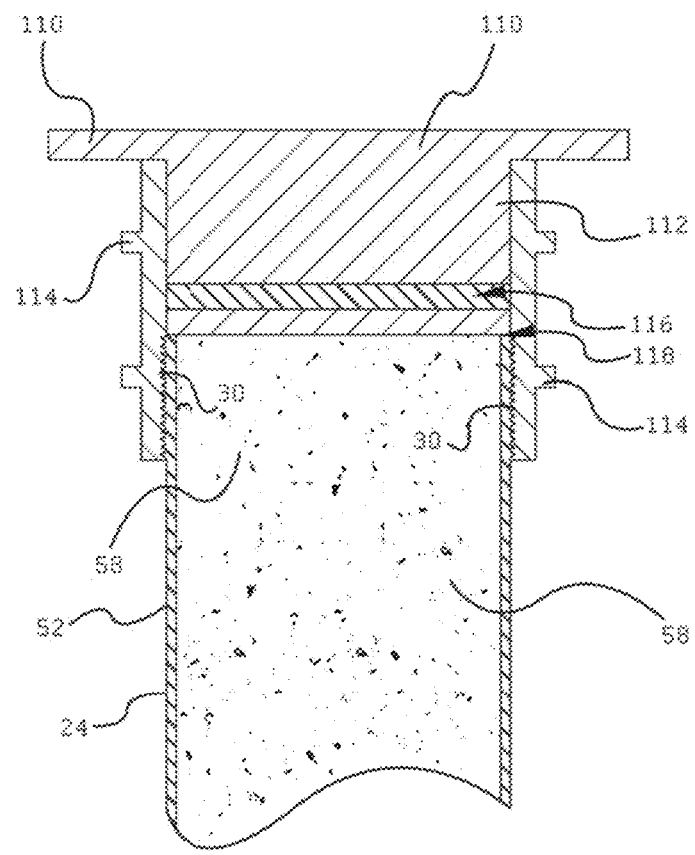
FIG. 17 is a vertical section of the pipe piling of FIG. 15.

Referring now to FIGS. 15-17, an exemplary PGD pile 24 with a test cap 104 (any PGD pile 24 to be dynamic load tested may be referred to as a test pipe pile) is drill driven so that a portion is exposed above grade 16. Specifically, FIGS. 15 and 16 illustrate an exemplary pattern 105 of sensor bores 106. FIG. 16 is a sectional view of the uppermost pile segment 52 of the PGD pile 24 (with the internal grout 58 omitted so not to obscure) along line 16-16 of FIG. 15 and illustrates an exemplary pattern 15 for the sensor bores 106. Temporary bolts 108 have been added to FIG. 16 to demonstrate that the temporary bolts 108 may extend into the interior of the PGD pile 24. FIG. 17 is a vertical section of the PGD pile 24 and test cap 104 of FIG. 15.

The test cap 104 comprises an strike plate 110, a pipe insert 112 attached to (or integral with) the underside of the strike plate 110 by welding or any other suitable means, and a connecting sleeve 114 also attached to the underside of the strike plate 110 by welding or any other suitable means. In one embodiment (not shown), the inner surface of the connecting sleeve 114 has threads to engage threads 30 of the uppermost pile segment 52 of PGD pile 24 in threaded engagement. The test cap 104 is temporarily placed over the top end 54 of the PGD pile 24, the pipe insert 112 extending into a hollow region internal of the PGD pile 24 to align the test cap 104 over the PGD pile 24 and to inhibit the test cap 104 from dislodging during testing. The strike plate 110 of the test cap 104 provides a platform for impact contact by a drop weight and readies the pipe pile 24 for dynamic load testing using the drop weight.

Sensor bores 106 are provided in the uppermost pile segment 52 of pipe pile 24 into which sensors (shown in FIG. 19) may be disposed to take readings during dynamic testing. From such readings, various characteristics of the pipe pile 24 (whether it is a PGD pile 24 or not) as drill driven, such as bearing capacity, dynamic pile tensile and compressive stresses (both axial and averaged over the pile cross section), and pile integrity, may be determined. Information from the readings may also be used to determine hammer performance parameters.

Although the sensor bores 106 may be drilled and tapped after the pipe pile 24 has been driven, in one embodiment, the pattern of sensor bores 106 are prepared in advance of the uppermost pile segment 52 being drill driven and filled with grout 58. With this embodiment, the sensor bores 106 are drilled and tapped prior to installation of the uppermost pile segment 52. Grease or silicone may be applied to temporary bolts 108 and the temporary bolts 108 may be tightened into each of the sensor bores 106. This may prevent the temporary bolts 108 from bonding with the grout 58 and creates a seal for the drilled sensor bores 106 so that grout 58 does not escape through the sensor bores 106. After the grout 58 cures the temporary bolts 108 may be removed and sensors (see FIG. 19) may then be inserted.

FIG. 16 is a sectional view of the PGD pile 24 along line 16-16 of FIG. 15 and illustrates an exemplary pattern 105 for the sensor bores 106. Temporary bolts 108 have been added to FIG. 16 to demonstrate that the temporary bolts 108 may extend into the interior of the PGD pile 24 so that the temporary bolts 108 may extend into the grout 58 (not shown so not to obscure). This enables the temporary bolts 108 to be removed so that sensors may be disposed within the grout 58 after it has been poured and cured.

Typically, the sensors used for dynamic load testing comprise at least one accelerometer and at least one strain gage. Although other types of sensors may be used to obtain additional or different readings. With the exemplary pattern 105 of sensor bores 106 of FIG. 15, two accelerometers and two to four strain gages are contemplated. The sensor bore 106 in the center of the pattern 105 may be used for an accelerometer (referred to herein as accelerometer 107), as well as the center for the pattern 105 (not visible) in the reverse side of the pipe pile 24. The accelerometer bore 107 is positioned a distance E from the top of the pipe pile 24 to the accelerometer bore 107 and a distance F from the accelerometer bore 107 to grade 16. In one embodiment, distance E is approximately two feet and distance F is approximately one foot. With this embodiment, the strain gage bores 109 are a distance G apart and substantially equidistant from the accelerometer bore 107. In the embodiment shown, distance G is approximately three inches. However, it should be understood that the pattern 105 and the distances E, F, and G may vary from what is disclosed in the depicted embodiment so long as desirable readings may be obtained during dynamic load testing. Persons of ordinary skill in the art will be able to readily determine alternative patterns 105 and distances E, F, and G. For example, FIG. 18 shows an alternative pattern 105.

To optimize the value of the information determined from the readings, there may be a space 116 between the underside of the test insert 112 and the top of the grout 58 elevation 118, as shown in FIG. 17. In one embodiment the elevation 118 may be below threads 30 so to avoid grout 58 inadvertently soiling the threads 30.

Figure 18:
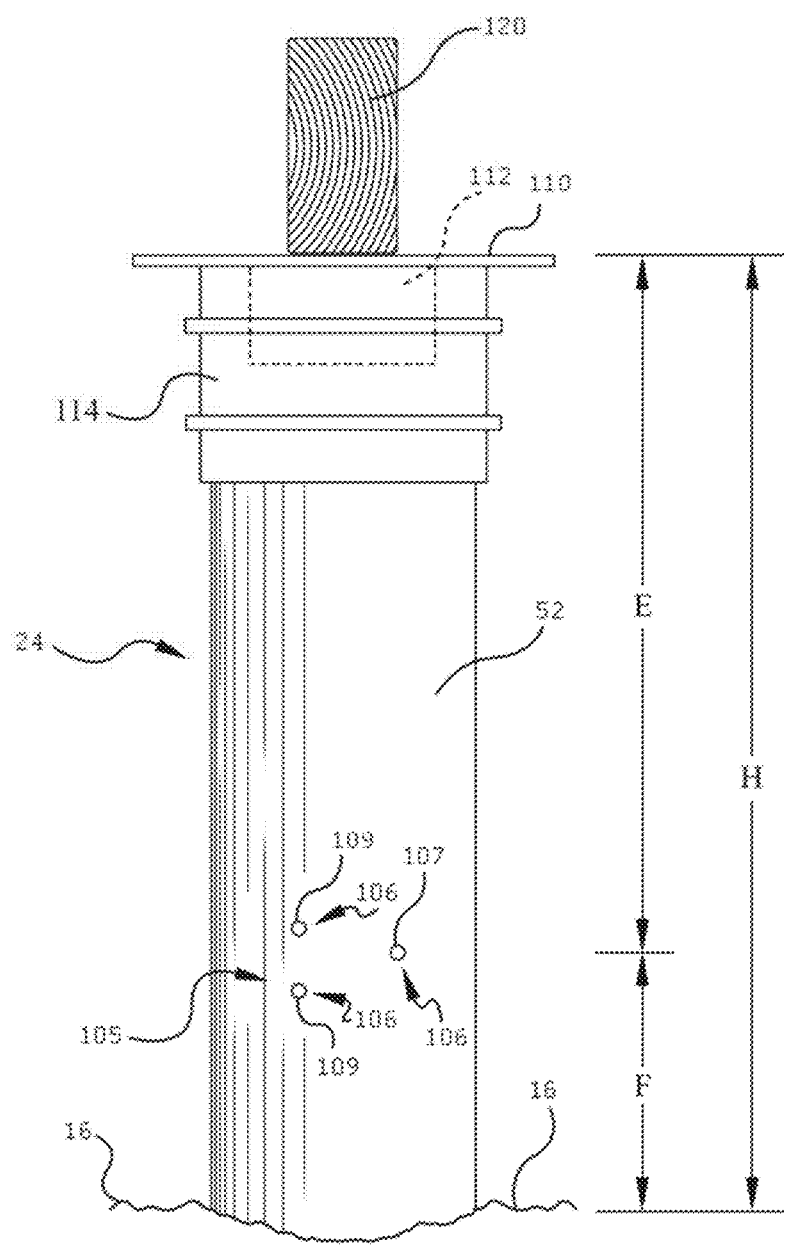
FIG. 18 is an elevation side view of an exemplary pipe piling with a test cap as disposed above grade and showing an alternative, exemplary sensor bore pattern and a cushioning block disposed on the test cap.

FIG. 18 is an elevation side view of an alternative exemplary pipe pie 24 with a test cap 104 as disposed above grade 16 and showing an alternative, exemplary sensor bore pattern 105 and a cushioning block 120 disposed on the test cap 104. Any suitable cushioning block 120 may be used. In some embodiments, a 4×4 or 4×6 block of wood or a plywood cushion may be used. If a plywood cushion is used, new sheets of plywood with a total thickness between approximately 2 to 6 inches (or any thickness determined by the on-site engineer) may be used.

The test pipe pile 24 should be free of mud, debris, concrete, etc. so to provide a smooth clean surface for attachment of sensors. The total height H of the pipe pile 24 should be at least 28 to 30 inches above grade so that the sensors may be positioned at least one diameter of the pipe pile 24 below the test cap 104.

Figure 19:
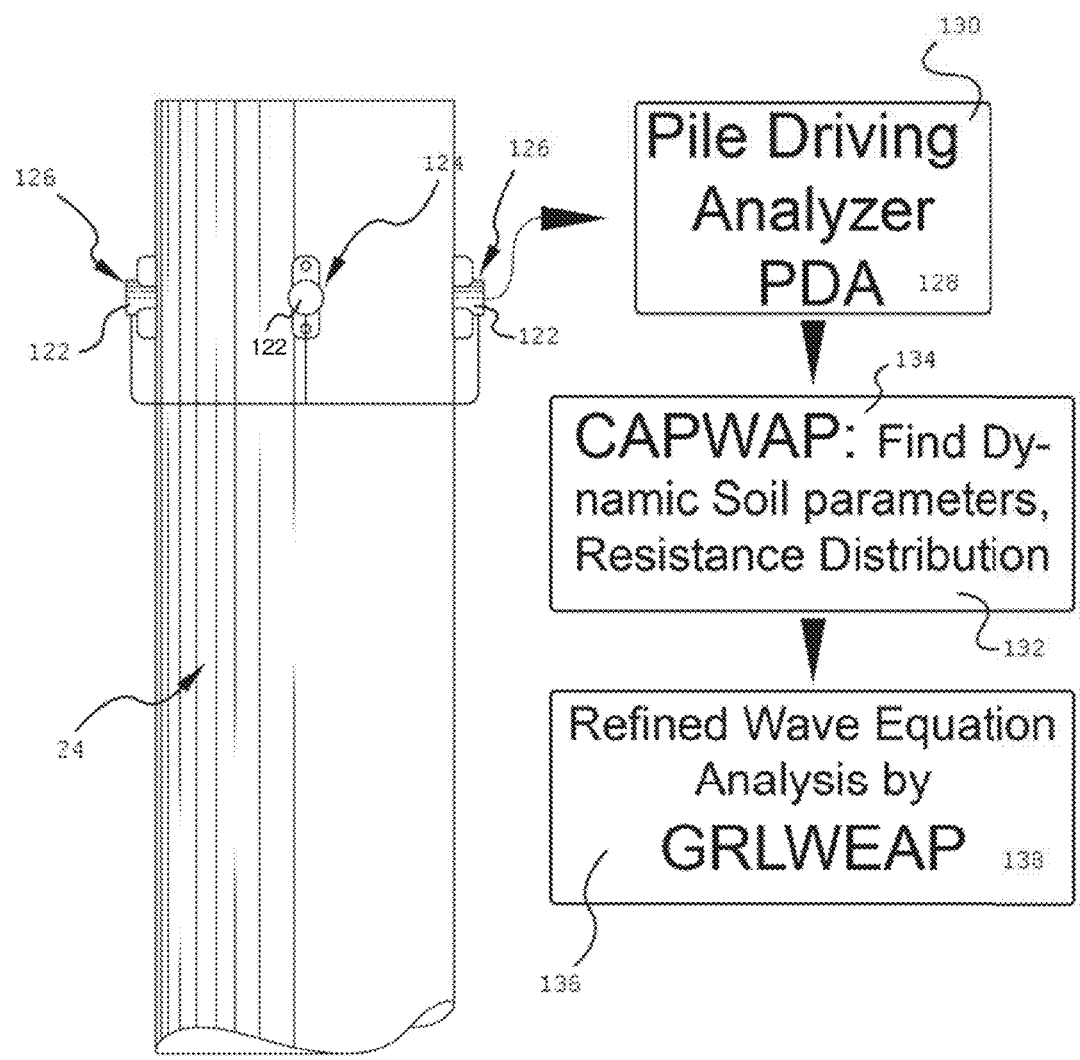
FIG. 19 is a combination elevation view of an exemplary pipe piling showing sensor placement and a schematic of steps for analyzing the information derived from the sensors.

FIG. 19 is a combination elevation view of an exemplary pipe pile 24 showing sensor 122 placement and a schematic of steps for analyzing the information derived from the sensors 122. In the exemplary embodiment depicted, the sensors 122 comprise at least two strain transducers 124 (one is obscured, but appears on the opposite side of the pipe pile 24) (also known as strain gages) and at least two accelerometers 126. With these sensors 122 properly placed, a Pile Driving Analyzer® 128 (commonly known as a PDA) may gather information from the sensors 122, process that information, and calculate and evaluate certain pipe pile 24 characteristics. The sensors 122 measure top pile force and velocity, and may measure other metrics depending on what types of sensors 122 are used. There are two principal objectives of high strain dynamic pile testing; namely, dynamic pile monitoring and dynamic load testing. Dynamic pile monitoring is conducted during installation to achieve a safe and economical pile installation. Dynamic load testing is principally an assessment of pile bearing capacity and is applicable to drill-driven pipe piles 24 during restrike by a drop weight (see FIG. 20). Box 130 depicts the PDA 128 extracting information from the sensors 122 and passing processed information to Box 132 where a Case Pile Wave Analysis Program (CAPWAP®) 134 computes soil resistance forces and their approximate distribution using the force and velocity data recorded by the PDA 128 in the field during the dynamic load testing. In some embodiments, the CAPWAP program, Version 2006 may be used. When using this version of the CAPWAP program 134, pertinent information derived may include an estimate of the soil resistance distribution, soil quake and damping factors, a simulated load-set graph, and an estimated shaft profile based on the force and velocity data. The dynamic stresses may either be directly measured at the top end of the pipe pile 24 by the PDA 128 or calculated by the PDA 128 for other locations along the pipe pile 24 based on the pile top measurements. A static load-set graph may be created based on the CAPWAP 134 calculated static resistance parameters and the elastic compression characteristics of the pipe pile 24 determined from the readings during dynamic load testing.

Heretofore, a procedure for dynamic load testing pipe piles has been done only under open construction conditions. Typically, restrike testing has involved quite heavy drop weights dropped significant distances, distances precluding testing under low overhead conditions. Hence, it was unknown whether pipe piles could be dynamic load tested under low-overhead conditions because of the belief that quite heavy drop weights dropped significant distances was believed necessary.

It has now been determined, however, that not only may the pipe piles be driven under low-overhead conditions, but such drill driven pipe piles may be dynamic load tested viably as well. Under the procedures disclosed herein, pipe piles 24 may be drill driven and dynamic load tested underneath a lifted house or building 10 to form a sturdy, dependable deep pile foundation. For example, although other similar low-overhead equipment 18 may be used, a Danuser model SM40 post driver drop hammer (see FIG. 20) which is skid-steer mounted has been used successfully. A Danuser model SM40 post drop hammer utilizes a 300 to 500 pound drop weight (a 500 pound drop weight was used for testing) with a fixed drop height of 40 inches was used to dynamically load test a 7 inch PGD pile 24 with acceptable results. For each hammer impact, the maximum compression stress near the top of the uppermost pile segment 52 at a location of the sensors 122 (see FIG. 19) was calculated by the PDA 128 using the average signal from the strain transducers 124. During testing, it was determined that the average shaft head compression stresses on the 7 inch diameter PGD pile 24 was 3.4 ksi.

The transferred energy was recorded for each hammer blow applied. Throughout testing, transferred energy averaged 0.41 kip-ft. The potential energy of the 500 pound drop weight dropping 40 inches is 1.67 kip-ft., making the energy transfer efficiency of the impact system average about 25%.

Changing soil conditions, pile response, or other factors can significantly change the amount of resistance that can be mobilized by a given drop weight. Consequently, it is prudent to use a 500 pound drop weight, although a lesser drop weight may be acceptable for many soil conditions given the type of pile being used.

A CAPWAP analysis was performed on impact number 12 for the pipe pile 24 tested. This impact was chosen because the collected data indicated an even impact across the pile section. The CAPWAP analysis of the data collected during impact number 12 indicated a mobilized capacity of 90 kips with approximately 79 kips in shaft resistance and 11 kips in end bearing. Further, the set was estimated to be just 1/32 inch over five impacts, therefore, it is likely that all of the soil resistance was not activated and the actual pile capacity was likely higher than 90 kips.

As a result of the testing and based on the quality of the collected data and the ability to obtain a reasonable match using existing CAPWAP software, it was determined that it is feasible to perform dynamic load testing on PGD pile foundations. The instrumentation, i.e., the strain transducers 124 and accelerometers 126, may be attached directly to the steel shell of the pipe pile 24 for testing and obtain accurate measurements of strain and acceleration for analysis. It was also determined that a grout build up section around the above-grade portion of the pipe pile 24 shaft is not necessary to perform the testing. The PGD piles 24 may be left as grout 58 filled steel shells during testing.

Additionally, a refined wave equation analysis may be performed at Box 136. Using information from Box 130 and Box 132, the GRLWEAP™ program 138 (written and developed by GRL Engineers, Inc., 30725 Aurora Road, Cleveland, Ohio 44139) calculates a relationship between bearing capacity, pile stress and blow count. This relationship is often called the bearing graph. Hence, once the blow count is known from pile installation logs, the bearing graph yields the bearing capacity. This approach requires no further measurements other than blow count.

After dynamic pile monitoring and/or dynamic load testing has been performed, the refined wave equation analysis may be performed by inputting the PDA 128 and CAPWAP 134 calculated parameters. With many of the dynamic parameters verified by dynamic tests, a more reliable basis for a safe and sufficient driving criterion is achieved. Importantly, such dynamic load testing may be performed under low-overhead conditions.

Figure 20:
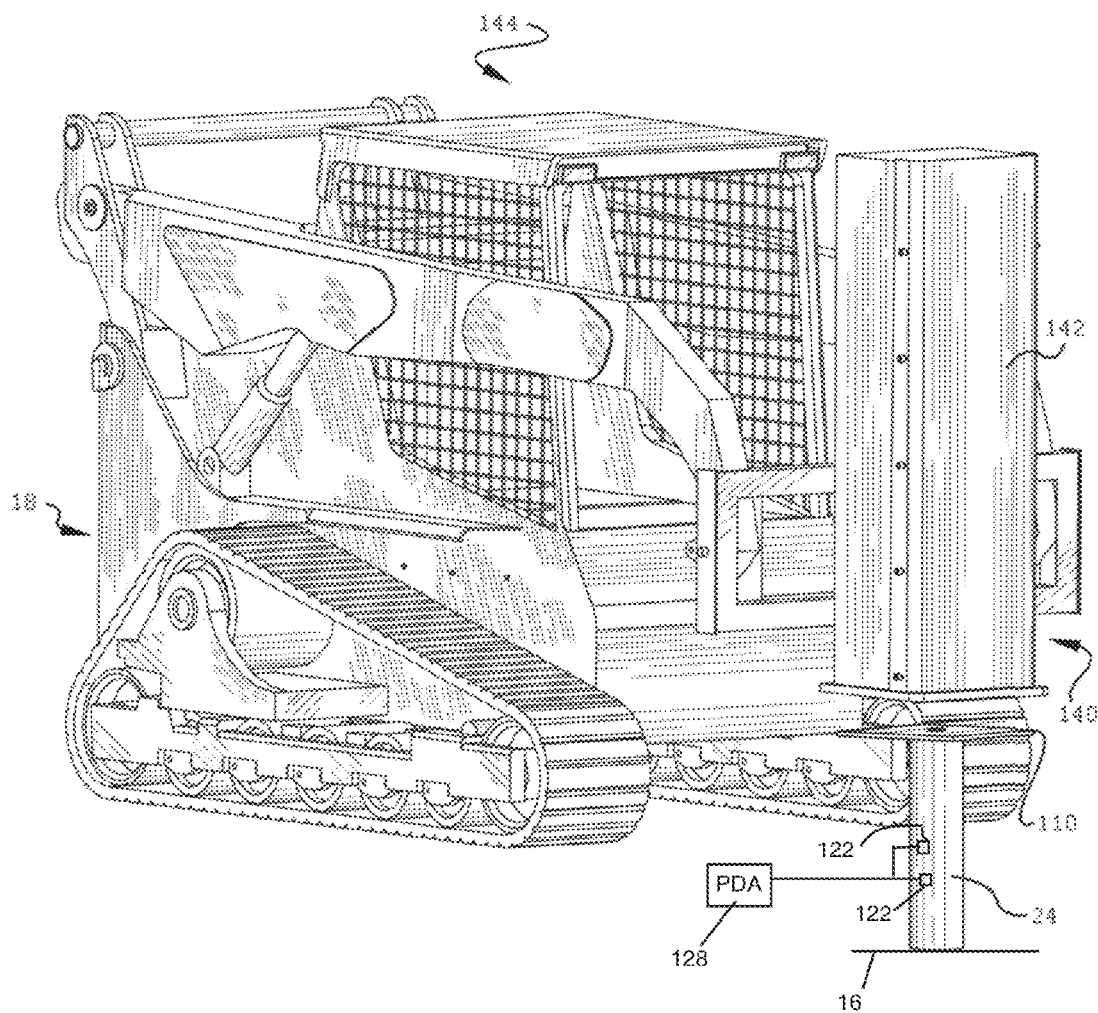
FIG. 20 is a perspective view of an exemplary low-overhead post driver used to apply impact force to a test pipe piling.

FIG. 20 shows an exemplary low-overhead post driver 140 that uses a drop weight attachment 142 to apply impact force to a test pipe pile 24 for dynamic load testing. FIG. 20 also shows schematically sensors 122 connected to the pipe pile 24 and a PDA 128. The cribbing stacks 12 and elevated building 10 are not shown in FIG. 20 so not to obscure the depiction provided. An exemplary post driver 140 with drop weight attachment 142 is the Danuser model SM40 post driver drop hammer. This exemplary drop hammer is a skid steer 144 mounted hammer 142 that may use a 300 to 500 pound drop weight (not visible, but within the drop weight attachment 142) with a fixed drop height of 40 inches. In one embodiment, a 500 pound drop weight may be used. Accordingly, dynamic load testing may be performed on any or all of the PGD piles 24 that have been drill driven beneath the elevated building 10 because the low-overhead post driver 140 may be positioned underneath the building 10 to perform the testing.

Figure 21:
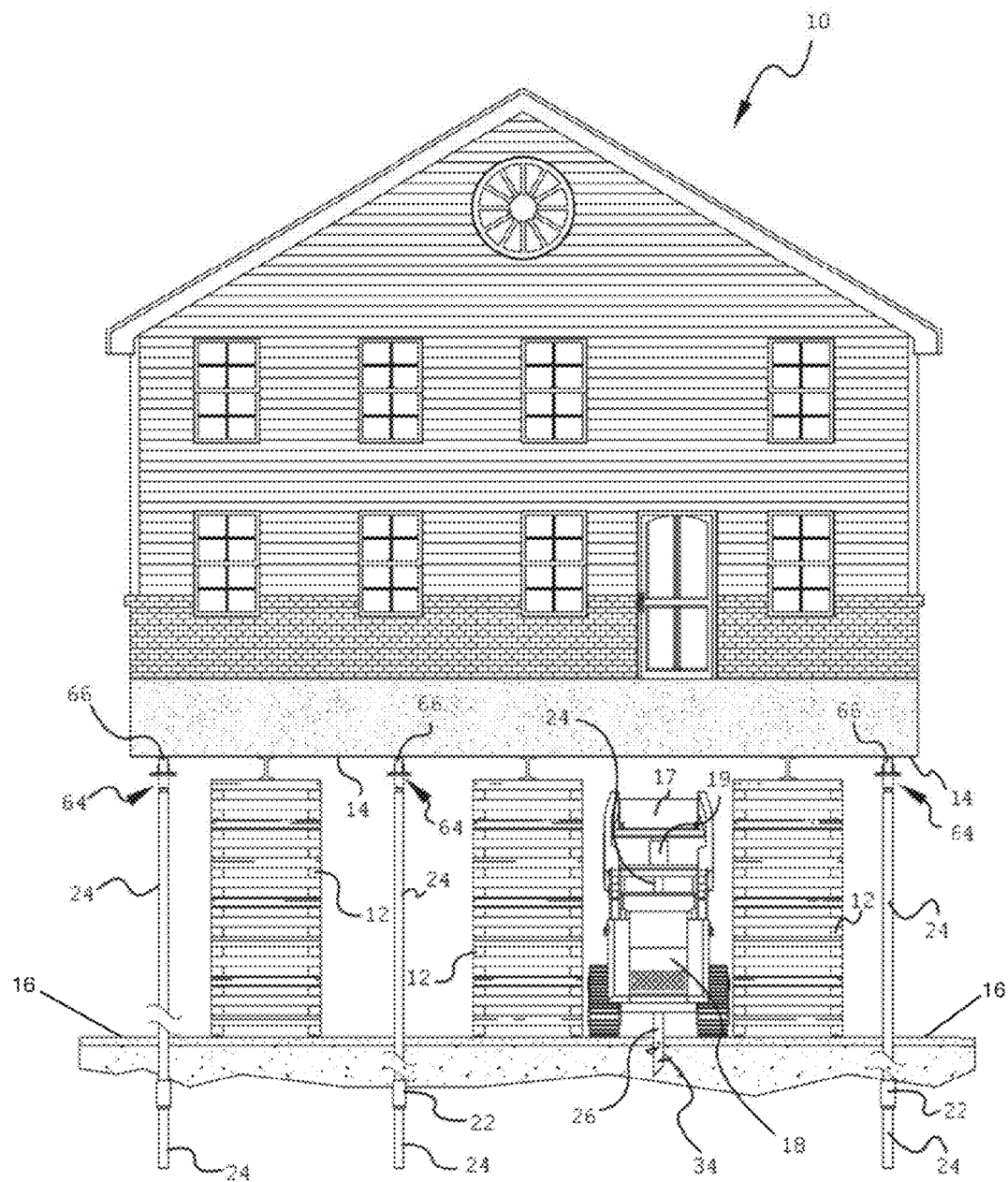
FIG. 21 is an elevation view of the home of FIGS. 1 and 7 that has been lifted onto support cribbing and showing a piece of low-overhead equipment in position to drive the final internal pipe piling.

FIG. 21 is an elevation view of the building 10 of FIGS. 1 and 7 that has been lifted onto support cribbing stacks 12 and showing low-overhead equipment 18 in position to drive the final internal pipe pile 24. Once the last pipe pile 24 has been driven, tested (if required), certified by the engineer, and connected to a support beam or girder 66, the cribbing stacks 12 may be removed so that the building 10 is fully supported by the array of pipe piles 24.

The pipe piles 24 may be finished in various ways to a desired aesthetically pleasing look. The exterior of any pipe pile 24 may be enclosed with wood framed or masonry enclosures that are compliant with local and/or FEMA regulations. The enclosure finishes may include but are not limited to manufactured stone veneer, brick, stucco, a synthetic stucco like exterior insulation and finishing systems (EIFS), epoxy coating and/or other wood framed enclosures with or without cladding.

While specific exemplary embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method for using low-overhead equipment to conduct dynamic load testing a test pipe pile for a deep pile foundation being constructed underneath an elevated, existing building, comprising the steps of:
 a) driving the test pipe pile using low-overhead equipment, the test pipe pile comprising a starter pile segment and an uppermost pile segment having a top end, the starter pile segment being disposed at one end and the uppermost pile segment being disposed at the opposite end, the starter pile segment creates disturbed soil surrounding the starter pile segment as the starter pile segment is driven;
 b) injecting grout under pressure into the test pipe pile during the driving thereof so that grout exits through a grout port to mix with the disturbed soil to encase the test pipe pile in a grout-soil mixture;
 c) leaving a portion of the uppermost pile segment of the test pipe pile above grade;
 d) attaching at least one of a plurality of sensors to the uppermost pile segment, the at least one of a plurality of sensors being disposed above grade and spaced a distance from the top end of the uppermost pile segment;
 e) disposing a strike plate over the top end of the of the uppermost pile segment;
 f) positioning a drop weight suspended from low-overhead equipment over the strike plate and underneath the elevated, existing building;
 g) dropping the drop weight to transfer impact force to the strike plate and the test pipe pile;
 h) sending information to a pile driving analyzer device, the information being characteristics of the test pipe pile derived from the sensors and resulting from the impact force;
 i) determining the acceptability of the test pipe pile for the deep pile foundation;
 j) connecting a pile cap to the top end of the uppermost pile segment; and
 k) securing the pile cap to the existing building.

2. A method as in claim 1 wherein the step of injecting grout under pressure is done continuously while the test pipe pile is being driven.

3. A method as in claim 1 further comprising the step of allowing the grout-soil mixture and grout within the test pipe pile to cure before dropping the drop weight.

4. A method as in claim 1 wherein the grout injected into the uppermost pile segment is injected to a predetermine height within the uppermost pile segment and the strike plate is spaced from the predetermined height of the grout within the uppermost pile segment.

5. A method as in claim 1 wherein the plurality of sensors comprise at least one strain transducer and at least one accelerometer.

6. A method as is claim 1 wherein the strike plate further comprises a pipe insert extending from the underside of the strike plate, the pipe insert nests within a hollow region defined by the top end of the uppermost pile segment.

7. A method as in claim 1 further comprises the step of disposing a cushion on the strike plate, the strike plate and cushion receive impact from the dropping of the drop weight.

8. A method as is claim 1 further comprises preparing the uppermost pile segment of the test pipe pile to receive sensors for dynamic load testing by pre-drilling a sensor bore for each of the plurality of sensors before the test pipe pile is driven.

9. A method as in claim 8 wherein the step of preparing the uppermost pile segment further comprises inserting a removable bolt into each pre-drilled sensor bore.

10. A method as in claim 9 wherein the step of preparing the uppermost pile segment further comprises applying a coating to least one removable bolt, the coating for facilitating the removal of the removable bolt before attaching the sensors.

11. A method for preparing an uppermost pile segment of a pipe pile to receive sensors for dynamic load testing the pipe pile to which the uppermost pile segment is connected after it is driven using low-overhead equipment underneath an elevated, existing building, comprising the steps of:
 a) before the uppermost pile segment of the pipe pile is driven, drilling a plurality of sensor bores in the uppermost pile segment spaced from a top end of the uppermost pile segment and disposed to be above grade when the pipe pile is driven;
 b) tapping at least one of the sensor bores to receive a removable bolt;
 c) inserting the removable bolt into the at least one of the sensor bores;
 d) driving the pipe pile using low-overhead equipment, the pipe pile comprising a starter pile segment and the uppermost pile segment, the starter pile segment creates disturbed soil surrounding the starter pile segment as the starter pile segment is driven;
 e) injecting grout under pressure into the pipe pile during the driving thereof so that grout exits through a grout port to mix with the disturbed soil to encase the pipe pile in a grout-soil mixture;
 f) leaving a portion of the uppermost pile segment of the pipe pile and the plurality of sensor bores above grade;
 g) allowing the grout-soil mixture and grout within the pipe pile to cure; and
 h) removing the removable bolt from the sensor bore so that the sensor bore may receive a sensor.

12. A method as in claim 11 wherein the step of injecting grout under pressure is done continuously while the pipe pile is being driven.

13. A method as in claim 11 further comprising the step of applying a coating the removable bolt, the coating for facilitating the removal of the removable bolt before attaching the sensor.

14. A method as in claim 11 wherein the plurality of sensor bores is disposed in a predetermined pattern.

15. A method as in claim 14 wherein the plurality of sensor bores comprise at least one sensor bore configured to receive a strain transducer and at least one sensor bore configured to receive an accelerometer.

16. A method as in claim 15 wherein the at least one sensor bore configured to receive a strain transducer is spaced a predetermined distance from the at least one sensor bore to receive an accelerometer.

17. A method as in claim 15 wherein the plurality of sensor bores comprise at least two sensor bores configured to receive the strain transducer and the sensor bores configured to receive the strain transducer are disposed 180° opposite each other.

18. A method as in claim 15 wherein the plurality of sensor bores comprise at least two sensor bores configured to receive the accelerometer and the sensor bores configured to receive the accelerometer are disposed 180° opposite each other.

19. A method for using low-overhead equipment to conduct dynamic load testing of a test pipe pile for a deep pile foundation being constructed underneath an elevated, existing building, comprising the steps of:
   a) before an uppermost pile segment of the test pipe pile is driven, drilling a plurality of sensor bores in the uppermost pile segment spaced from a top end of the uppermost pile segment and disposed to be above grade when the test pipe pile is driven;
   b) tapping at least one of the sensor bores to receive a removable bolt;
   c) inserting the removable bolt into the at least one of the sensor bores;
   d) applying a coating to the removable bolt, the coating for facilitating the removal of the removable bolt before attaching a sensor;
   e) driving the test pipe pile using low-overhead equipment, the test pipe pile comprising a starter pile segment and the uppermost pile segment having a top end, the starter pile segment is disposed at one end and the uppermost pile segment is disposed the opposite end, the starter pile segment creates disturbed soil surrounding the starter pile segment as the starter pile segment is driven;
   f) injecting grout under pressure into the test pipe pile during the driving thereof so that grout exits through a grout port to mix with the disturbed soil to encase the test pipe pile in a grout-soil mixture;
   g) leaving a portion of the uppermost pile segment of the test pipe pile above grade;
   h) allowing the grout-soil mixture and grout within the test pipe pile to cure;
   i) removing the removable bolt from the sensor bore so that the sensor bore may receive the sensor;
   j) attaching at least one of a plurality of sensors to the uppermost pile segment, the at least one of a plurality of sensors being disposed above grade and spaced a distance from the top end of the uppermost pile segment;
   k) disposing a strike plate over the top end of the of the uppermost pile segment;
   l) positioning a drop weight suspended from low-overhead equipment over the strike plate and underneath the elevated, existing building;
   m) dropping the drop weight to transfer impact force to the strike plate and the test pipe pile;
   n) sending information to a pile driving analyzer device, the information being characteristics of the test pipe pile derived from the sensors and resulting from the impact force;
   o) determining the acceptability of the test pipe pile for the deep pile foundation;
   p) connecting a pile cap to the top end of the uppermost pile segment; and
   q) securing the pile cap to the existing building.

20. A method as in claim 19 wherein the plurality of sensor bores comprise at least one sensor bore configured to receive a strain transducer and at least one sensor bore configured to receive an accelerometer.

* * * * *